US010973526B2

(12) United States Patent
Nair et al.

(10) Patent No.: US 10,973,526 B2
(45) Date of Patent: Apr. 13, 2021

(54) CUSTOMIZED ENDOVASCULAR DEVICES AND METHODS PERTAINING THERETO

(71) Applicants: Priya Nair, Tempe, AZ (US); David H. Frakes, Scottsdale, AZ (US); Ryan Hess, Tempe, AZ (US)

(72) Inventors: Priya Nair, Tempe, AZ (US); David H. Frakes, Scottsdale, AZ (US); Ryan Hess, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 425 days.

(21) Appl. No.: 15/726,186

(22) Filed: Oct. 5, 2017

(65) Prior Publication Data

US 2018/0092690 A1 Apr. 5, 2018

Related U.S. Application Data

(60) Provisional application No. 62/404,541, filed on Oct. 5, 2016.

(51) Int. Cl.
  *A61B 17/12* (2006.01)
  *A61F 2/06* (2013.01)
(52) U.S. Cl.
  CPC .. *A61B 17/12145* (2013.01); *A61B 17/12113* (2013.01); *A61B 17/12172* (2013.01); *A61F 2/06* (2013.01)
(58) Field of Classification Search
  CPC .......... A61B 17/12113; A61B 17/1214; A61B 17/12145
  See application file for complete search history.

(56) References Cited

U.S. PATENT DOCUMENTS

| 2004/0116997 A1* | 6/2004 | Taylor | A61F 2/07 623/1.11 |
| 2009/0297582 A1* | 12/2009 | Meyer | A61B 17/12022 424/423 |
| 2013/0116722 A1* | 5/2013 | Aboytes | A61M 29/00 606/198 |

OTHER PUBLICATIONS

Babiker, M. et al., "Finite element modeling of embolic coil deployment: Multifactor characterization of treatment effects on cerebral aneurysm hemodynamics", Journal of Biomechanics, 2013, 46(16), pp. 2809-2816.
Dell, S., "Asymptomatic cerebral aneurysm: assessment of its risk of rupture.", Neurosurgery, Feb. 1982, 10(2), pp. 162-166.
Eberhardt, K. et al., "O-14-196: CT-angiography (CTA) in patients with intracranial aneurysms. Comparison with MR-angiography (MRA) and Digital Subtraction Angiography (DSA)", Clinical Neurology and Neurosurgery, Jul. 1997, vol. 99, suppl. I., pp. s98-s99.

(Continued)

*Primary Examiner* — Melanie R Tyson
(74) *Attorney, Agent, or Firm* — Lewis Roca Rothgerber Christie LLP

(57) ABSTRACT

Patient-specific 3D complex coils and methods of making and using such coils, including custom fixtures for the manufacture of such coils. Such patient-specific 3D complex coils improve treatment outcomes for cerebral aneurysm repair. The aneurysm may be an aneurysm in a specific patient and/or population of patients having a similar aneurysm shape and size.

8 Claims, 21 Drawing Sheets

(56) References Cited

OTHER PUBLICATIONS

Emory University, "Aneurisk Web: The Aneurisk dataset repository", Aneurisk website, 2013, https://web.archive.org/web/20130915212854/http://ecm2.mathcs.emory.edu/aneuriskweb/index (screenshot from Sep. 15, 2013 obtained from archive.org).
Gupta, V. et al., "Nitinol thin film three-dimensional devices—Fabrication and applications", Proceedings of the International Conference on Shape Memory and Superelasitc Technologies, ASM International, 2004, pp. 639-650.
Hanley, M., "AngioCalc—Cerebral and Peripheral Aneurysm Calculator: Background", AngioCalc website, 2009, https://web.archive.org/web/20090624144652/http://www.angiocalc.com:80/about.php (screenshot from Jun. 24, 2009 obtained from archive.org).
Lu, Y. et al., "Hold time effects on low cycle fatigue behavior of HAYNES 230® superalloy at high temperatures", Materials Science and Engineering: A, Nov. 2005 (2005), 409(1-2), pp. 282-291.
Morgan, N. et al., "Taking the art out of smart! Forming processes and durability issues for the application of NiTi shape memory alloys in medical devices.", Medical Device Materials: Proceedings of the Materials and Processes for Medical Devices Conference, ASM International, 2004, pp. 247-252.
Pelton, A. et al., "The physical metallurgy of nitinol for medical applications", Journal of Metals, May 2003, 55(5), pp. 33-37.
Smith, S. et al., "Shape Setting Nitinol.", Medical Device Materials: Proceedings of the Materials and Processes for Medical Devices Conference, ASM International, 2004, pp. 266-270.
Utela, B. et al., "Shape training of nitinol wire using three-dimensional printing (3DP) fixtures", 18th Solid Freeform Fabrication Symposium, SFF, Aug. 6-8, 2007, 2007, pp. 284-291.
White, L. et al., "Coils in a nutshell: a review of coil physical properties", American Journal of Neuroradiology, Aug. 2008 (available online Apr. 2008), 29(7), pp. 1242-1246.
Wiebers, D., "Unruptured intracranial aneurysms: natural history, clinical outcome, and risks of surgical and endovascular treatment", The Lancet, Jul. 2003, 362(9378), pp. 103-110.
Xiang, J. et al., "Newtonian viscosity model could overestimate wall shear stress in intracranial aneurysm domes and underestimate rupture risk.", Journal of Neurointerventional Surgery, Sep. 2011, pp. 1-7.

* cited by examiner

Complex Coil

Helical Coil

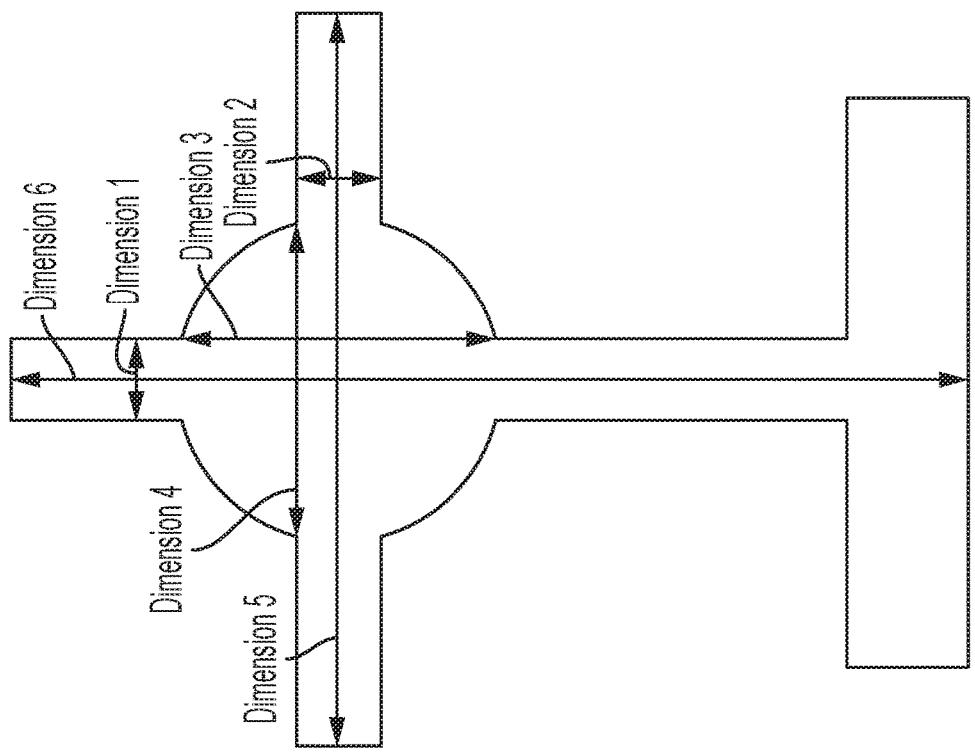

CUSTOMIZED ENDOVASCULAR DEVICES AND METHODS PERTAINING THERETO

CROSS-REFERENCE TO RELATED APPLICATION

This application claims priority to U.S. Provisional Application No. 62/404,541 filed Oct. 5, 2016, the content of which is incorporated herein by reference in its entirety.

STATEMENT REGARDING FEDERALLY SPONSORED RESEARCH OR DEVELOPMENT

None.

BACKGROUND

The present disclosure relates generally to the fields of biomedical engineering, specifically medical device design. More particularly, it concerns the design of endovascular coils for aneurysm repair.

A cerebral aneurysm (CA) is a bulge in a blood vessel of the brain caused by weakening in the vessel wall. CA's pose a high risk of rupturing, causing intracranial hemorrhaging, which is often referred to as a hemorrhagic stroke. Common patient outcomes from intracranial hemorrhaging are temporary or permanent brain damage or death. CA's often do not cause any symptoms prior to rupturing, and can burst without warning. CA's are typically discovered through routine imaging during diagnosis of other conditions due to their lack of symptoms. Once discovered, a variety of imaging techniques are used to create a radiographic study of the aneurysm and understand its morphology. These techniques include computerized tomography angiography (CTA), magnetic resonance angiography (MRA), digital subtraction angiography (DSA), ultrasound (US), or a combination of multiple types of radiography. CA's can have a wide variety of morphologies, although common shapes are spheroidal, ellipsoidal, or multi-lobed in nature.

An objective of CA treatment involves isolating the aneurysm from blood flow to promote intra-aneurysmal thrombosis, thereby reducing the risk of rupture. Over time, vascular remodeling at the aneurysm neck (where the aneurysm attaches to the parent vessel) results in permanent separation of the aneurysm from circulation. CA's can be treated via surgical or endovascular techniques. Surgical treatment involves isolating the aneurysm from blood flow by pinching the base of the aneurysm using surgical clips. This treatment method involves invasive, risky neurosurgery with prolonged recovery times but high success rates.

Endovascular treatment techniques involve navigating a catheter containing a device to the aneurysm site via the vasculature. Endovascular coiling is a popular treatment technique used in clinical practice where a series of small, flexible coils fill the inside of the aneurysm to isolate or reduce blood flow into the aneurysm. However, not all aneurysms can be treated endovascularly due to their morphology, which may not allow a coil to fit securely inside without risk of detachment. Endovascular coiling is considered the gold standard of aneurysm treatment due to decreased procedural risk and recovery period for patients.

High variability exists within the practice of endovascular coiling, and treatment is largely determined on a patient-specific basis by a neurointerventional radiologist. Biocompatible metal alloys, such as platinum/tungsten, are most widely used to manufacture coils. These coils are manufactured by tightly coiling platinum/tungsten wire into a helix around a mandrill and heat setting it to set the shape of the coil. The wire itself is considered to be the primary structure of the coil and the tightly wound helical coil is considered to be the secondary structure of the coil. FIGS. 1A-C show examples of endovascular coils. The diameters of the primary and secondary structures are represented by $D_1$ and $D_2$, respectively, shown in FIG. 1A. The secondary structure of the coil is then wound around a mandrill of larger diameter to form a tertiary helical structure as shown in FIG. 1B, or around a fixture to create a complex tertiary structure as shown in FIG. 1C and heat set again. The diameter of a helical tertiary structure denoted as $D_3$ in FIG. 1A. Although the tertiary structure is unwound as the coil is integrated into a microcatheter, the coil resumes its tertiary structure as it is ejected from the microcatheter. These coils are mass-manufactured by multiple medical device companies, and then medical professionals take their pick of which coils to use based on the individual aneurysm's shape, size, location, and a number of other factors. Resources exist to assist physicians in determining volume of the aneurysm, packing density of the coils required based on the volume, and what packing density will be achieved through use of different coils. Because they are so tightly wound, the secondary structure of these coils is treated as a solid cylinder for the purpose of calculating packing density, which is shown below in equation 1:

$$\text{Packing Density} = \frac{\text{coil volume}}{\text{aneurysm volume}} \times 100 \text{ where coil volume} = D_2 \times \text{coil length} \quad \text{Equation 1}$$

These coils have varying shapes and degrees of stiffness depending on their function as a framing coil, which lines the outside of the aneurysm, or packing coil, which fills the interior of the aneurysm. The stiffness of the coil is determined by the chemical composition of the wire used, as well as diameters $D_1$, $D_2$, and $D_3$.

Therefore, a main limitation of the current coil designs is sub-optimal aneurysm occlusion for atypical aneurysm morphologies, which can eventually lead to aneurysm recanalization or recurrence. Thus, currently commercially available spherical coils can result in the use of assistive treatment techniques for aneurysms of varying shapes.

SUMMARY

The present disclosure relates to patient-specific 3D complex coils and methods of making and using such coils. These patient-specific 3D complex coils improve treatment outcomes for aneurysm repair. Specifically, the invention provides at least the advantages of a patient-specific device design that provides optimal aneurysmal occlusion and reduces long-term complications.

Customizing treatment for each individual aneurysm allows a doctor to accommodate variability related to the size and shape of aneurysms. The first step toward customizing treatment methods for aneurysms is through modeling of aneurysms. Through modeling, treatment methods can be adjusted based on individual aneurysm shapes, sizes, and blood vessel physical properties such as torsion tolerances. By starting with digital modeling using modern radiographic studies, individual aneurysms can be mapped and studied from the inside out without performing any exploratory surgery and further expanded or otherwise modified in order to observe them more closely. The second step toward customizing treatment is fabrication of customized coils. Such coils may be made of a shape memory alloy material. In some embodiments, a shape memory alloy such as nitinol was used to create the coils. Nitinol is an alloy of nickel and titanium that is highly biocompatible, superelastic, and can be configured to a wide range of shapes due to temperature-dependent shape memory properties. The disclosed embodiments may be especially useful in the imaging, modeling, and treatment of cerebral aneurysms but other types of aneurysms may be imaged, modeled, and treated as well.

In some embodiments, a system for creating a 3-dimensional (3D) representations of one or more aneurysms includes: a computer system comprising at least one processor configured to: receive one or more images of a blood vessel; enable an identification of one or more aneurysms in the one or more images of the blood vessel; enable a segmentation of the one or more images, the segmentation enabling an isolation of the one or more aneurysms; enable a creation of one or more 3D aneurysm models based on the segmentation, the one or more 3D aneurysm models comprising one or more aneurysm characteristics; and enable the sending of 3D representation data corresponding to the one or more 3D aneurysm models, the 3D representation data configured to enable a creation of one or more physical 3D representations of the one or more aneurysms. In some embodiments, the one or more images of the blood vessel comprise one or more maximum intensity projection (MIP) images, the MIP images configured to enable 3D spatial visualization of the blood vessel. In some embodiments, the one or more 3D aneurysm models comprise one or more orthographic projections in stereolithographic format. In some embodiments, the one or more physical 3D representations comprise 3D printed models. In some embodiments, the one or more images of the blood vessel comprise one or more computerized tomography angiography (CTA), magnetic resonance angiography (MRA), digital subtraction angiography (DSA), and ultrasound images. In some embodiments, the one or more aneurysm characteristics comprise one or more of geometric characteristics and surface characteristics of the one or more aneurysms. In some embodiments, the one or more 3D aneurysm models comprise one or more cylinders each disposed at one or more predetermined dimensions of the one or more 3D aneurysm models.

In some embodiments, a method of creating 3-dimensional (3D) representations of one or more aneurysms includes: receiving, by a computer system comprising at least one processor, one or more images of a blood vessel; enabling, by the computer system, an identification of one or more aneurysms in the one or more images of the blood vessel; enabling, by the computer system, a segmentation of the one or more images, the segmentation enabling an isolation of the one or more aneurysms; enabling, by the computer system, a creation of one or more 3D aneurysm models based on the segmentation, the one or more 3D aneurysm models comprising one or more aneurysm characteristics; and enabling, by the computer system, the sending of 3D representation data corresponding to the one or more 3D aneurysm models, the 3D representation data configured to enable a creation of one or more physical 3D representations of the one or more aneurysms.

In some embodiments, a patient-specific endovascular coil is adapted for the treatment of an aneurysm in a specific patient and/or population of patients having a similar aneurysm shape and size. In some embodiments, patient-specific endovascular coil is further defined as a 3D complex coil comprising wire. In some embodiments, the wire comprises a shape memory alloy. In some embodiments, the wire comprises nitinol, platinum:tungsten, and/or platinum:iridium. In some embodiments, the patient-specific endovascular coil is further defined as being produced by a method comprising 3D printing or a casting technique. In some embodiments, the patient-specific endovascular coil is further defined as being produced for a specific patient based on the modeling of data from that patient.

In some embodiments, a method of making a patient-specific endovascular coil adapted for the treatment of an aneurysm in a specific patient and/or population of patients having a similar aneurysm shape and size includes: obtaining information on a specific aneurysm or set of similar aneurysms; designing a patient-specific endovascular coil fixture using the information; making a physical representation of the fixture; and manufacturing the endovascular coil using the fixture. In some embodiments, the information comprises at least one of aneurysm shape, size, blood vessel physical property, and/or blood vessel torsion tolerance. In some embodiments, the information is obtained from digital modeling and/or radiographic study. In some embodiments, the design is by a computer design process. In some embodiments, the computer design process is an AutoCAD design process. In some embodiments, the making is by 3D printing or a casting technique. In some embodiments, the patient-specific endovascular coil comprises nitinol, platinum:tungsten, and/or platinum:iridium. In some embodiments, the fixture is used to create a tertiary coil shape of the patient-specific endovascular coil using a heat-setting process. In some embodiments, the physical representation of the fixture comprises a physical representation of the specific aneurysm or set of similar aneurysms and includes one or more anchors each disposed at one or more predetermined dimensions of the fixture. In some embodiments, the manufacturing comprises winding a wire comprising nitinol, platinum:tungsten, and/or platinum:iridium around the fixture into the shape of the specific aneurysm or set of similar aneurysms, wherein the wire is secured to the fixture by the one or more anchors. In some embodiments, the manufacturing further comprises: annealing the wire; cooling the wire; and removing the wire from the fixture, the wire maintaining the shape of the specific aneurysm or set of similar aneurysms. In some embodiments, a method of treating an aneurysm in a patient includes: obtaining a patient-specific endovascular coil; and inserting the coil into the patient. In some embodiments, the inserting is by a microcatheter.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

FIG. 10 depicts evaluation dimensions of the idealized aneurysm fixtures shown in FIGS. 9A-B.

DETAILED DESCRIPTION

Figure 1C:
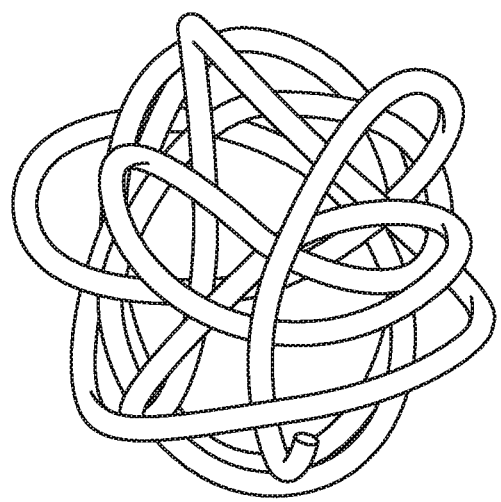
FIGS. 1A-C depict exemplary endovascular coils that can be used to repair aneurysms.
Figure 1B:
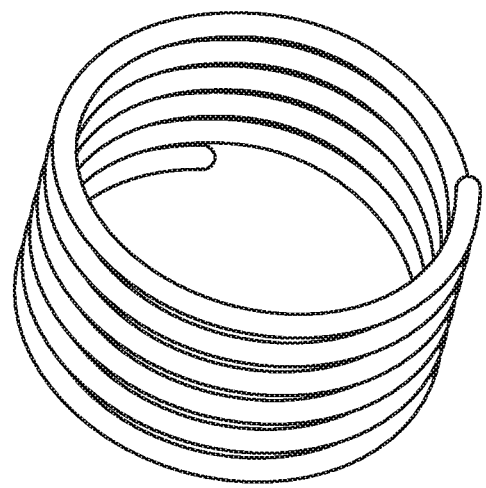
Figure 1A:
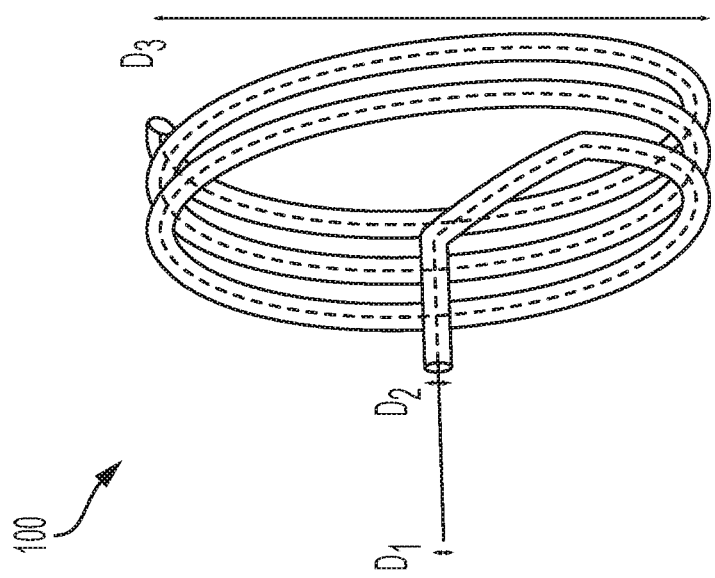

Endovascular cerebral aneurysm repair with coils is minimally invasive. During this technique, a catheter containing the device is navigated to the aneurysm site under fluoroscopic guidance. A series of flexible coils are then deployed within the aneurysm sac to promote intra-aneurysmal clotting, eventually leading to complete isolation of the aneurysm from circulation. Coil type, size and amount used for treatment is determined based on the aneurysmal volume. However, clinical aneurysmal volume calculation often relies on linear measurements, while the aneurysm geometry is not thoroughly taken into account. Due to this, aneurysms of complex morphology (i.e., aneurysms that are not spherical or elliptical in shape) often encounter difficulty in treatment with endovascular coils.

A purpose of the disclosed systems and methods is to engineer customized cerebral aneurysm fixtures for endovascular coil design. The fixture can be used for "heat setting" or annealing the coil wires (usually an alloy comprising of platinum and tungsten) such that it takes a specific shape.

Structurally, endovascular coils have three distinct configurations: primary, secondary and tertiary. The primary configuration is the wire with diameters ranging from 0.00175 to 0.003 inches. The primary wire is tightly wound into the secondary configuration with helical winds (like a guitar string). The helical diameter ranges from 0.010 to 0.020 inches. The secondary wire configuration is then wound along buttons located on fixtures that determine the tertiary coil shape. Once the tertiary coil shape is configured, the fixture along with the coil is heat-set for about 30 minutes between 550-650° C. The wire thickness and helical diameter (primary and secondary configurations, respectively) determine the coils stiffness, while the tertiary configuration influences the coil packing density. The shape set coils are then packaged into microcatheters.

The fixture design used for shape setting the wires drives the tertiary coil shape, that determines coil distribution within the aneurysm sac. Helical coils use cylindrical fixtures, while complex 3D coils use a spherical fixture that is attached to a substrate by a small cylinder, resembling a "lollipop." Commercially manufactured coils use the aforementioned fixture shapes, usually made of stainless steel during the coil manufacturing process.

The disclosed systems and methods provide for design of customized fixtures based on patient-specific aneurysm geometry that would take into account different cerebral aneurysm morphologies. This enables the design of endovascular coils on a patient-specific basis. The first step toward manufacturing the fixtures involves selecting a material that provides for creation of fixture that is easily moldable and can withstand the high temperatures required for shape setting. The next step involves consulting a library of anatomically realistic cerebral aneurysms, which are then used to shape the fixtures with the help of advanced 3D printing and casting techniques. The fixtures would then be manufactured with a biocompatible and shape memory alloy such as nitinol, platinum:tungsten, and/or platinum:iridium.

Figure 2:
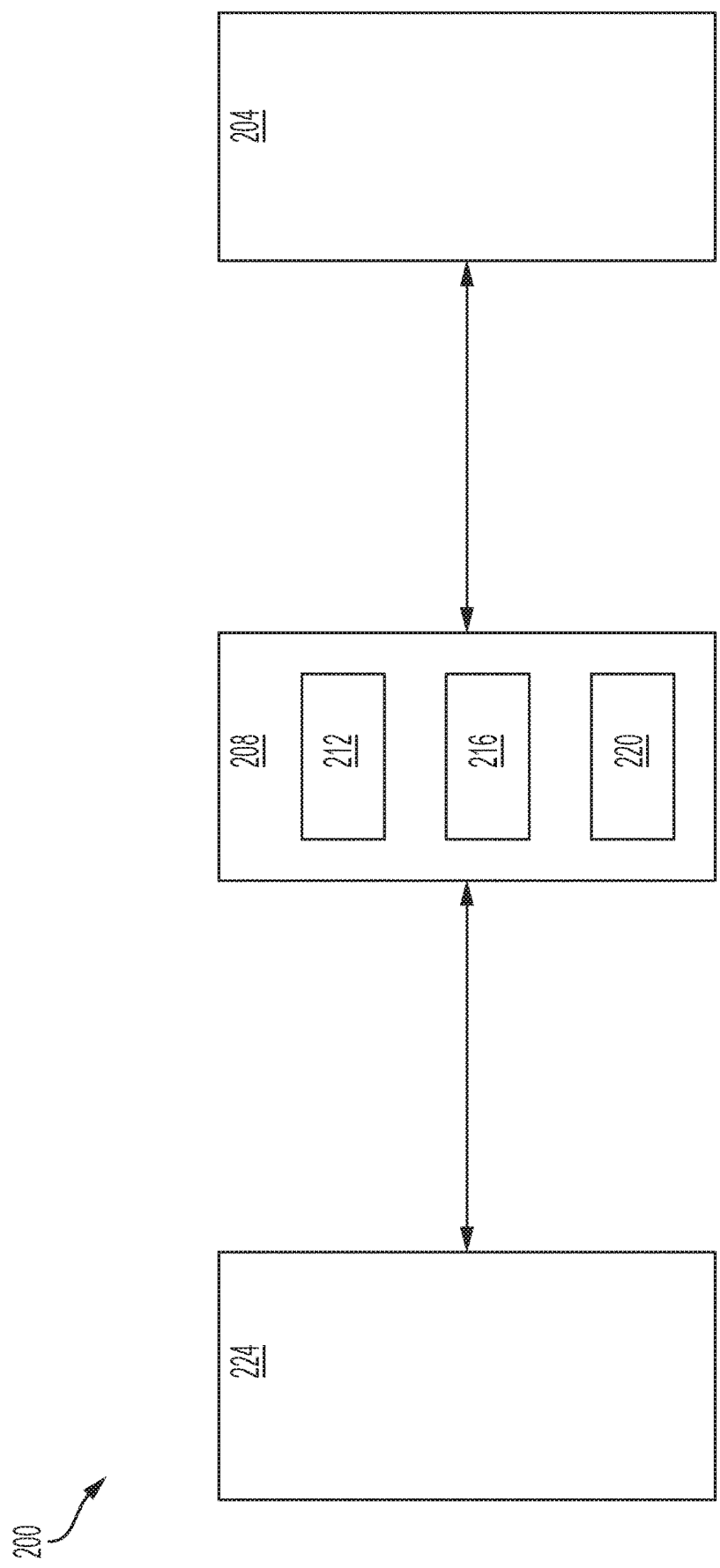
FIG. 2 depicts an exemplary 3D imaging and aneurysm representation system according to an embodiment of the disclosure.

Referring now to the drawings, FIG. 2 depicts an exemplary 3D imaging and aneurysm representation system 200 according to an embodiment of the disclosure. In the embodiment shown, an imaging device 204 may be provided. The imaging device 204 may provide imaging via CTA, MRA, DSA, US, or other types of radiographic imaging and can be configured to provide both 2D and 3D imaging capabilities. A processing device 208 may be capable of receiving 2D and/or 3D images taken by the imaging device. Processing device 208 may be a part of a computer system that may include standard components such as a hard drive, monitor, printer, keyboard, and mouse, among others, that may enable a user to interact with the processing device 208. In the embodiment shown, processing device 208 may include one or more of a segmentation application 212, a 3D modeling application 216, and one or more databases 220. In some embodiments, segmentation application 212 may be configured to receive one or more images from imaging device 204, segment the one or more images into one or more regions, and enable a selection of one or more regions. These selected regions may be referred to as regions of interest (ROI). In some embodiments, the selection of ROI may be done automatically by processing device 208. In some embodiments, the selection of ROI may be done by a user.

In some embodiments, the selected ROI may be exported by segmentation application 212 and imported into 3D modeling application 216. In some embodiments, 3D modeling application 216 may generate one or more 3D models of the selected ROI. In some embodiments, the selected ROI may correspond to one or more aneurysms. In some embodiments, the selected ROI may be converted to stereolithography (.stl) format and/or displayed as 3D orthographic models to enable orthographic views. The one or more 3D models may be displayed to a user and 3D modeling application 216 may enable a user to view and manipulate the one or more 3D models. In some embodiments, image manipulation capabilities may include capabilities to rotate, zoom, mark, color, and select the one or more models. In some embodiments, one or more databases 220 may contain information corresponding to various aneurysm characteristics. Examples of these aneurysm characteristics may include shape or geometric characteristics, size characteristics, topographical characteristics, volume characteristics, surface area characteristics and the like. In the embodiment shown, processing device 208 may be configured to send data corresponding to the one or more 3D models to a 3D printing device 224. 3D printing device 224 may create a 3D physical representation of the received one or more 3D models.

Figure 3:
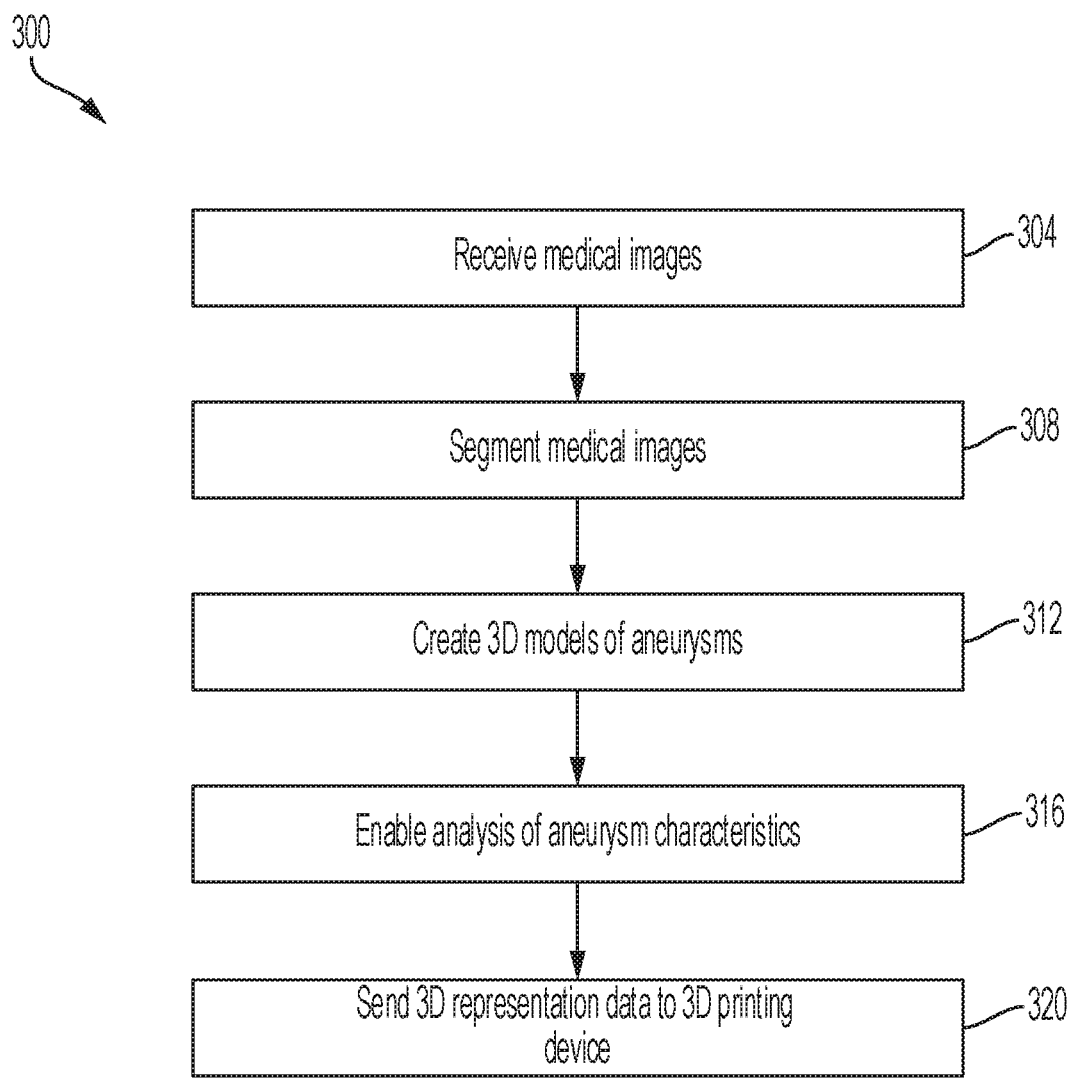
FIG. 3 depicts an exemplary method for creating 3D representations of aneurysms according to an embodiment of the disclosure.

FIG. 3 depicts an exemplary method 300 for creating 3D representations of aneurysms according to an embodiment of the disclosure. In one embodiment of the disclosure, method 300 may be implemented by system 200. In the embodiment shown in FIG. 3, method 300 may begin at step 304 by receiving one or more 2D or 3D images. Method 300 may continue at step 308 by segmenting the received one or more images. In some embodiments, segmenting step 308 may include segmenting the one or more images into one or more ROI. The one or more ROI may correspond to one or more aneurysms. In some embodiments, aneurysms may be selected in 3D format using an MIP 3D file. In this way, the computer system and/or a user may manipulate a 3D object in 2D space and may select one or more ROI. Isolating aneurysms from 3D MRI images may allow for a better appreciation of both the geometric and surface characteristics of aneurysms. In a 2D view, a variety of signals may influence pixel intensities that may result in pixel misclassification. Isolating aneurysms from 3D images may overcome some of these shortcomings of 2D aneurysm isolation.

Method 300 may continue at step 312 by creating one or more 3D models of aneurysms. In some embodiments, the one or more 3D aneurysm models may be orthographic models or MIP models. Method 300 may continue at step 316 by enabling the analysis of one or more aneurysm characteristics. For example, a computer system may analyze the one or more aneurysm models to determine one or more characteristics of the aneurysm. A user may also analyze the one or more aneurysm models by interacting with the computer system. In some embodiments, metadata may be used to denote a type or category of an aneurysm characteristic. In some embodiments, aneurysm characteristics may include geometric characteristics. Geometric characteristics may provide insights into a size and shape of an aneurysm. Examples of geometric characteristics may include aneurysm symmetry/asymmetry, surface morphology (e.g., amorphous, ovoid), the existence of lobes and/or protrusions, and other shape characteristics (e.g., tapered/wedge, spherocylindrical). In some embodiments, aneurysm characteristics may include surface characteristics. Surface characteristics may provide insights into aneurysm surface traits and aneurysm properties not associated with geometry. Examples of surface characteristics may include the existence of surface microstructures, surface topography (e.g., steepness/sheerness of surface peaks and valleys), surface irregularities, and a non-uniform distribution of mass of the aneurysm. In some embodiments, the computer system may engage in machine learning to generate descriptive surface, shape, and signal characteristics from the entire aneurysm or sections within aneurysms in order to more efficiently and accurately classify aneurysm types. Method 300 may continue at step 320 by sending data corresponding to the one or more 3D aneurysm models to a 3D printing device. Based on the received data, the 3D printing device may create a 3D physical representation or printed model of an aneurysm. In some embodiments, the 3D physical representation may exhibit one or more of the aneurysm characteristics.

Figure 4A:
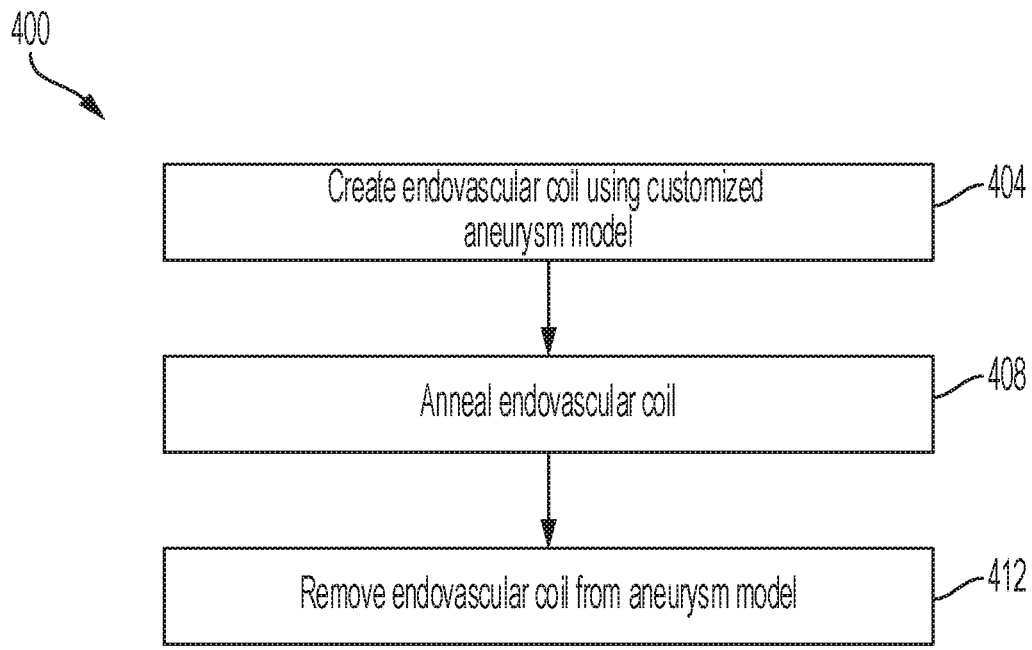
FIGS. 4A-B depict exemplary methods for creating customized endovascular coils according to an embodiment of the disclosure.
Figure 4B:
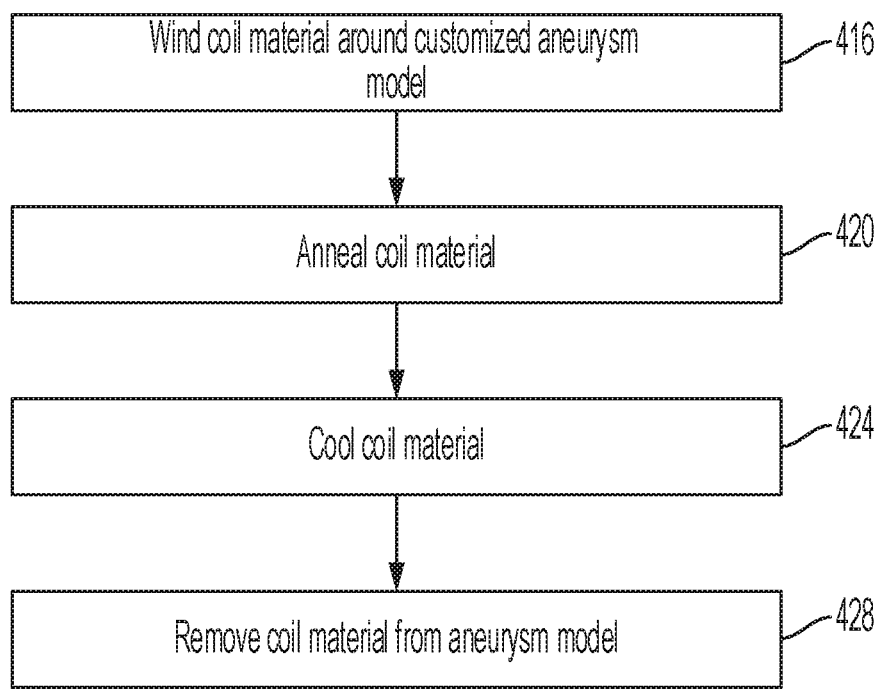

FIGS. 4A-B depict exemplary methods 400 for creating customized endovascular coils for aneurysms according to an embodiment of the disclosure. In the embodiment shown in FIG. 4A, method 400 may begin at step 404 by creating an endovascular coil using a customized aneurysm model. In some embodiments, the customized aneurysm model may be a 3D printed physical representation of an aneurysm created by 3D printing device 224 from 3D representation data sent at step 320 of method 300. In some embodiments, the 3D printed physical representation of an aneurysm may be an aneurysm fixture. Method 400 may continue at step 408 by heating or annealing the endovascular coil once the coil is in the shape of the customized aneurysm model. Method 400 may continue at step 412 by removing the annealed endovascular coil from the aneurysm model. The method steps shown in FIG. 4B may be performed in addition to or instead of the method steps shown in FIG. 4A. In the embodiment shown in FIG. 4B, method 400 may begin at step 416 by winding a coil material around a customized aneurysm model. In some embodiments, the coil material can be a wire made of a biocompatible and shape memory alloy such as nitinol, platinum:tungsten, and/or platinum:iridium. The coil material can be wound around the model to create a customized helical or complex coil in the shape of the aneurysm model. Method 400 may continue at step 420 by heating or annealing the coil material. This step may be performed by heating both the model and the coil material wrapped around the model. Method 400 may continue at step 424 by cooling the coil material. By cooling the coil, the coil may be in an elastic state to enable removal from the fixture. Method 400 may end at step 428 by removing the coil material from the aneurysm model. This step may be performed by unwrapping the cooled annealed coil from the model or removing the model from within the wrapped annealed coil. In some embodiments, upon removing the coil material, an unwrapped coil may modify its shape to return to the wrapped shape of the aneurysm model due to the properties of a shape memory alloy. In this way, the coil can be customized to the shape of the aneurysm and can more efficiently be inserted into the aneurysm to repair the aneurysm.

Figure 5C:
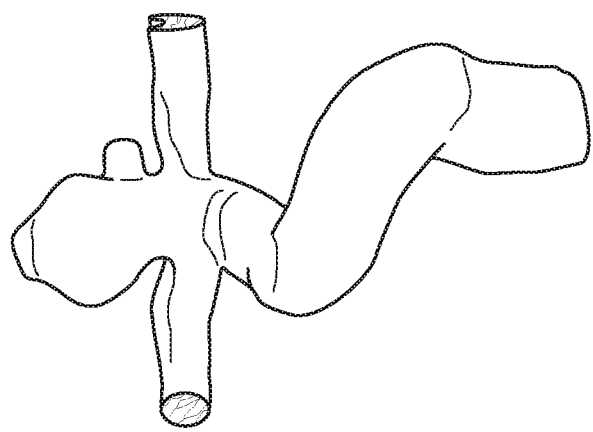
FIGS. 5A-C depict exemplary 3D aneurysm models that may be constructed according to an embodiment of the disclosure.
Figure 5B:
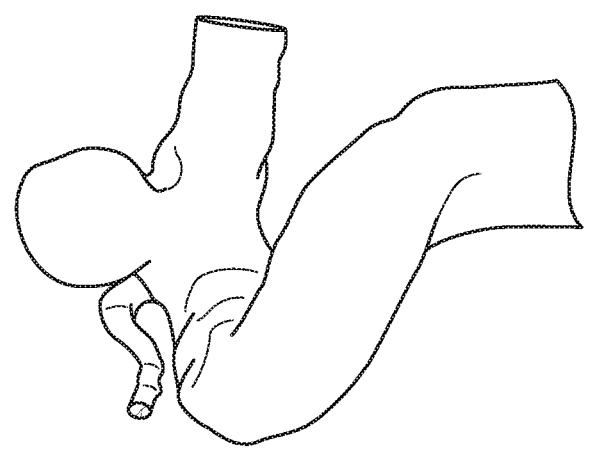
Figure 5A:
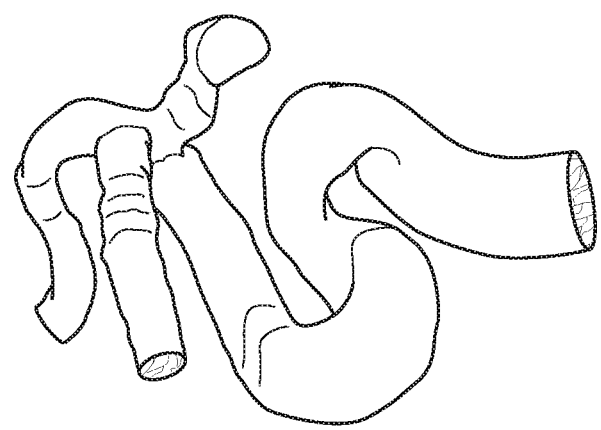

FIGS. 5A-C illustrate digital image renderings 500 of different cerebral aneurysms showing the variance in morphology between aneurysms and the need for customized endovascular coils to repair these differently shaped aneurysms. In the disclosed embodiments, to begin aneurysm modeling, aneurysm images and/or models can be received from an imaging device or aneurysm geometries can be gathered from an online database of digital aneurysm images and/or models for a particular patient. This digital repository can offer 3D surface models with centerline data, as well as additional information for some aneurysm models, such as computerized flowmetry models. The 3D models can be offered in DICOM files, which are used in radiographic image processing programs, as well as STL files, which can be uploaded to CAD programs to modify the 3D model structure.

Figure 6:
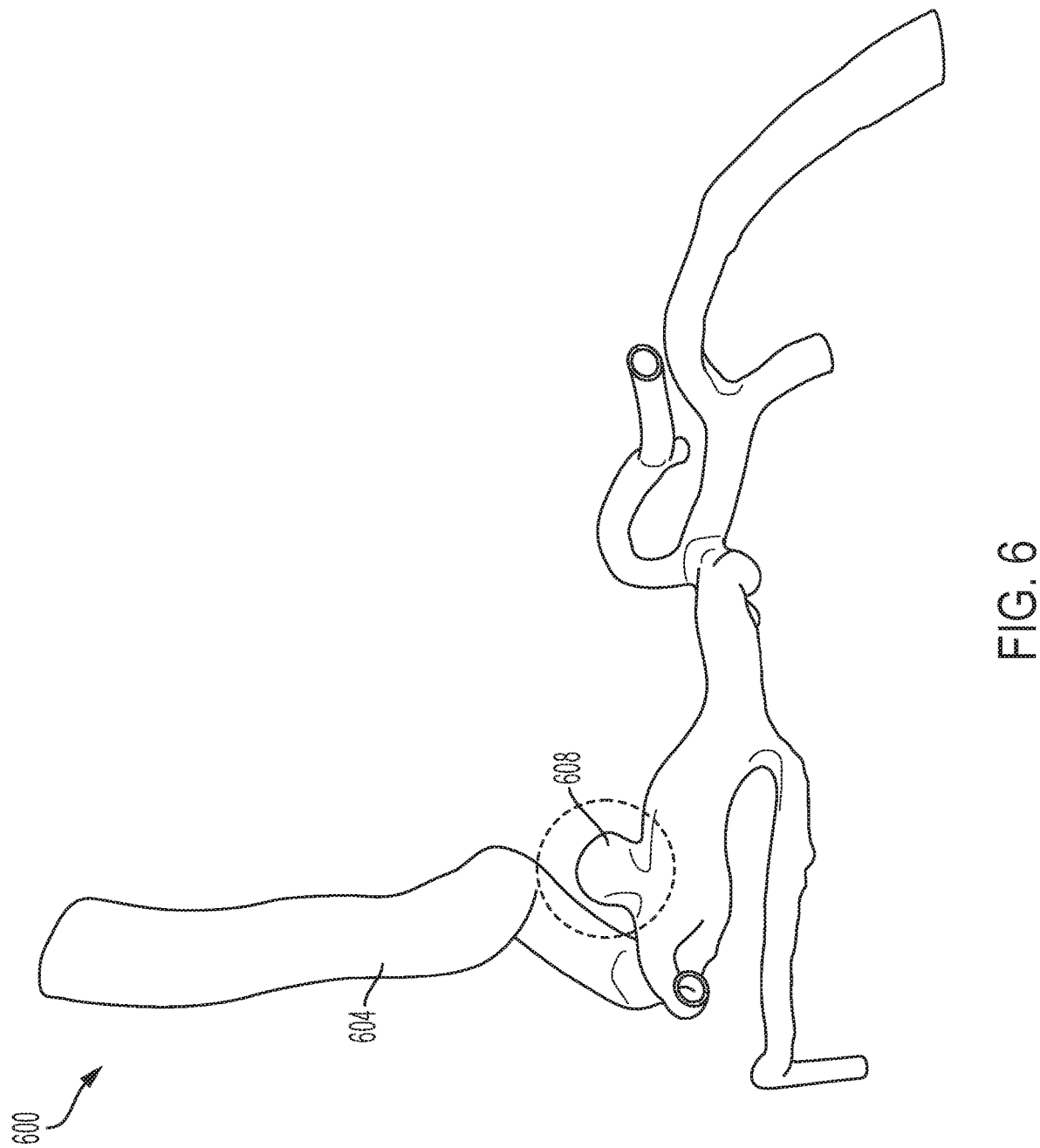
FIG. 6 depicts an exemplary 3D blood vessel image that may be constructed according to an embodiment of the disclosure.

The STL files of these models can be downloaded and imported into software for viewing and editing. An example of an unmodified digital image 600 of a blood vessel 604 containing an aneurysm 608 is shown in FIG. 6. In the embodiment shown, the aneurysm 608 can be isolated from the surrounding vasculature by virtually removing blood vessels 604 distal to the neck of the aneurysm. The neck of the aneurysm can then be reduced by carefully removing the portion of the neck that flares outward into the surrounding vasculature. The empty space can be filled and slightly extruded and rounded to minimize sharp angles and maximize a contact surface with the wire to be coiled around the model once printed. FIG. 7A shows digital models 700 of aneurysm 608 isolated from blood vessel 604. In some embodiments, this isolation can be performed manually by a user manipulating unmodified digital image 600 within viewing and editing software. In some embodiments, the system can bypass creation of an unmodified digital image of an entire blood vessel by performing segmentation of the medical aneurysm image received from the imaging device, isolating the aneurysm from the blood vessel, and creating a 3D digital model of the aneurysm such as that shown in FIG. 7 using the methods previously disclosed.

Figure 7B:
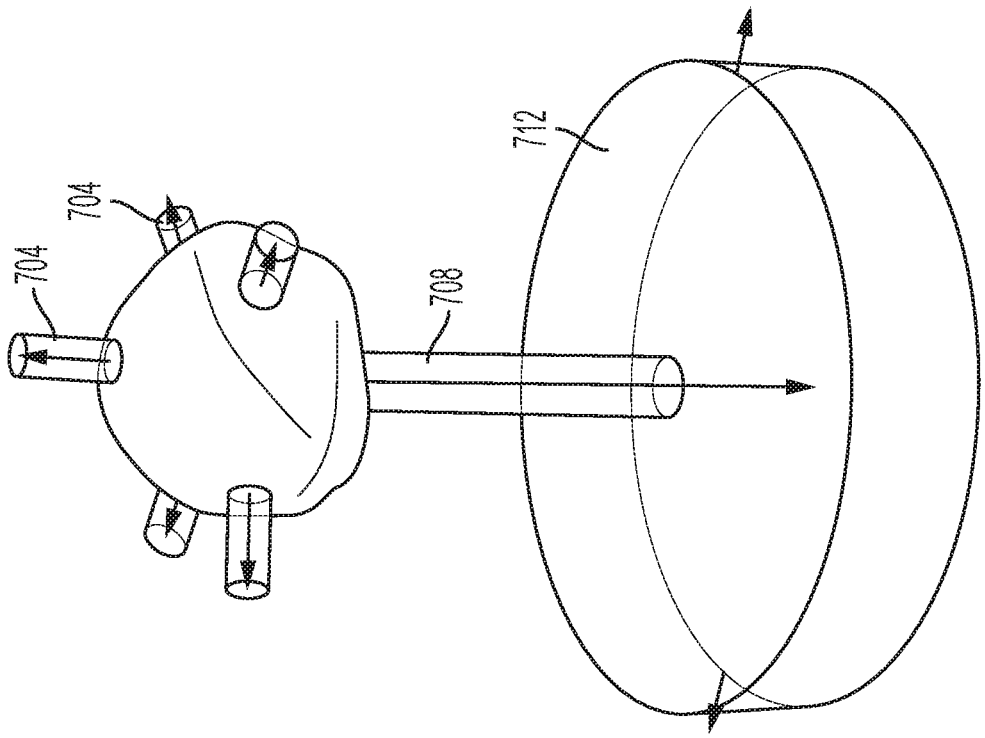
FIGS. 7A-B depict exemplary 3D isolated aneurysm models that may be constructed according to an embodiment of the disclosure.
Figure 7A:
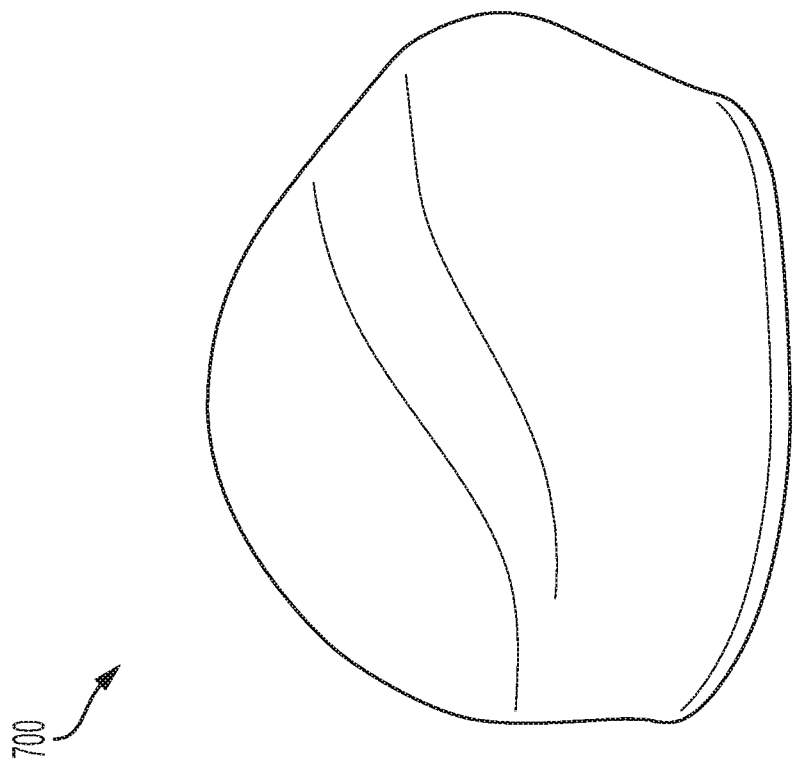

FIG. 7B shows the aneurysm model shown in FIG. 7A modified to include cylinders 704 disposed at particular dimensions of the aneurysm. In the embodiment shown, cylinders 704 can be extruded at various points around the aneurysm model at angles normal to the surface to the model to serve as anchors where wire can be tightly wound around to secure the wires across the model. The anchors can be added with consistent spacing so that various dimensions of the aneurysm can be wrapped in wire without the anchors being located in such close proximity that they would complicate coiling. In the embodiment shown in FIG. 7B, a central cylinder 708 can be disposed at a portion of each model representing the aneurysm's opening into the blood vessel. This central cylinder can be extended and attached to a wide, flat base 712 to serve as a foundation to support the model off the ground when a 3D representation of the model is created.

Figure 8:
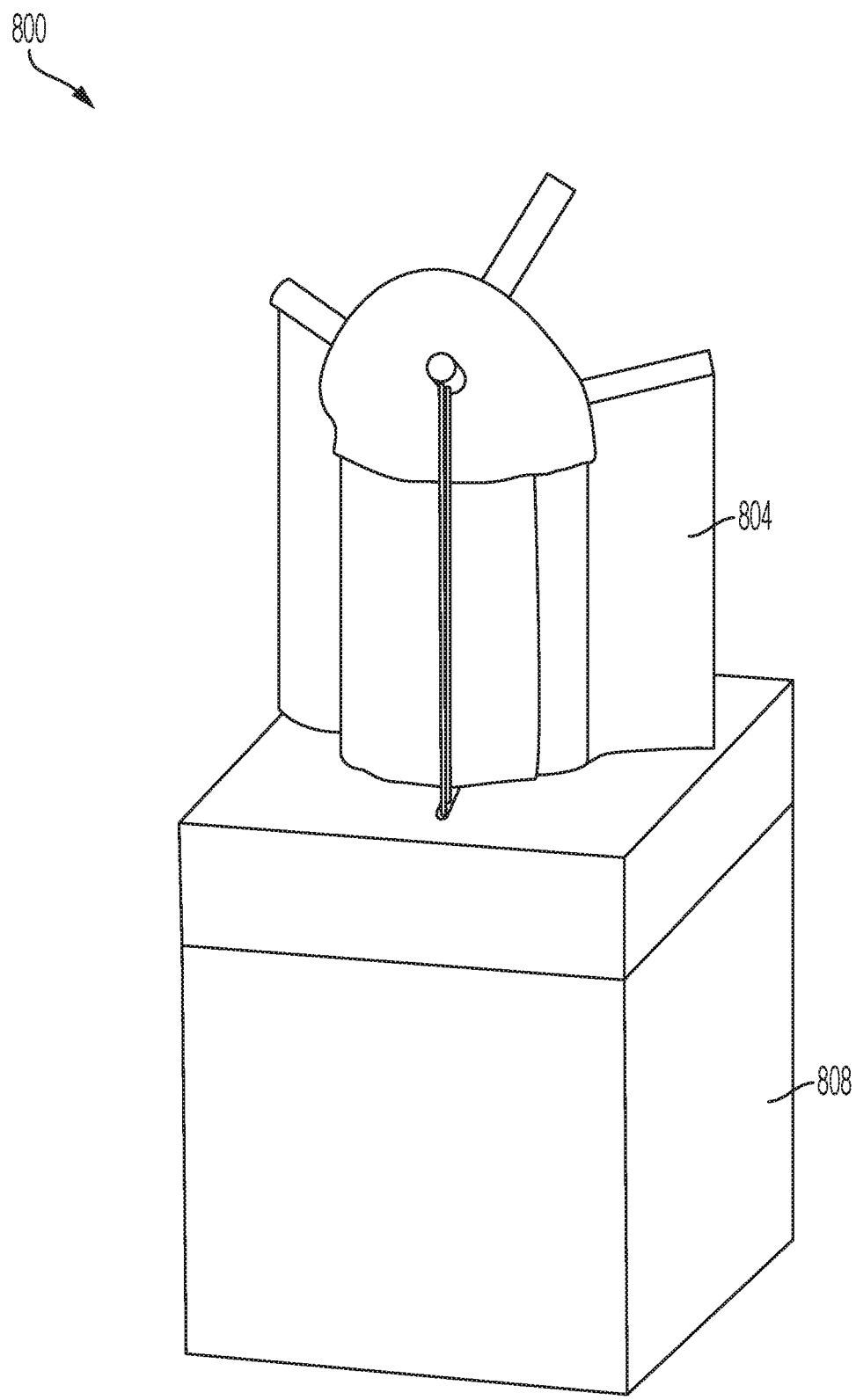
FIG. 8 depicts an exemplary image of a 3D printed model according to an embodiment of the disclosure.

In some embodiments, the 3D models can be exported as STL files to a 3D printing device for fabrication. Machining of stainless steel is often used to manufacture simple, standard fixtures that can be used to make non-customized coils. However, complex fixtures structures such as those needed for custom coil creating cannot be machined. 3D printing can be used to create complex, irregular shapes that machining cannot. Various materials can be used to fabricate the aneurysm fixtures. For example, stainless steel, stainless steel alloys infused with other metals such as bronze, and/or other superalloys can be used. In some embodiments, the fixture image file (e.g., STL file) can be loaded into a software application that can generate a 3D printer representation of the fixture from the STL file of the fixture. The software application can be calibrated to the 3D printer in order to generate support structures 804 and a baseplate 808 where needed for the printing process and to slice the model in order to determine powder layer thickness and the pathway of the laser. FIG. 8 shows an image 800 of the fixture shown in FIG. 7B with support structures added. The powder in the printer can be leveled using a powder deposition blade before the printing process begins and the fixture can be printed by the 3D printer. Following completion of the printing process, the printed fixture can be removed from the printed baseplate, supporting structures can be removed, and the fixture can be filed as necessary.

Figure 9B:
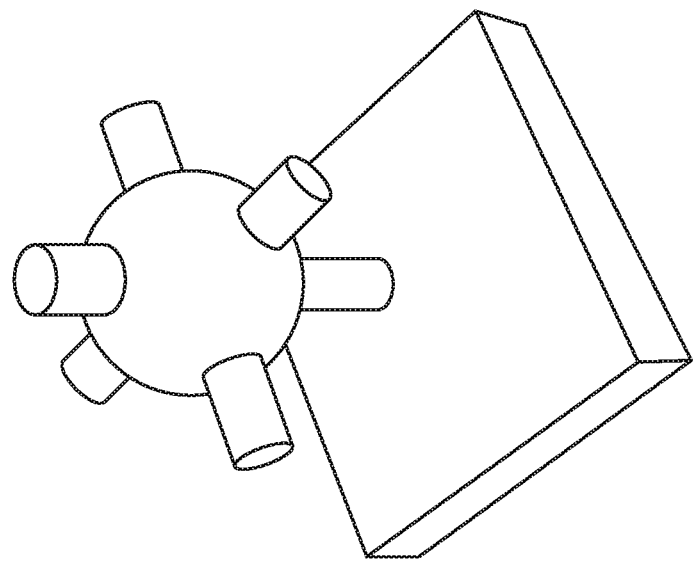
FIGS. 9A-B depict exemplary idealized aneurysm fixtures that may be constructed according to an embodiment of the disclosure.
Figure 9A:
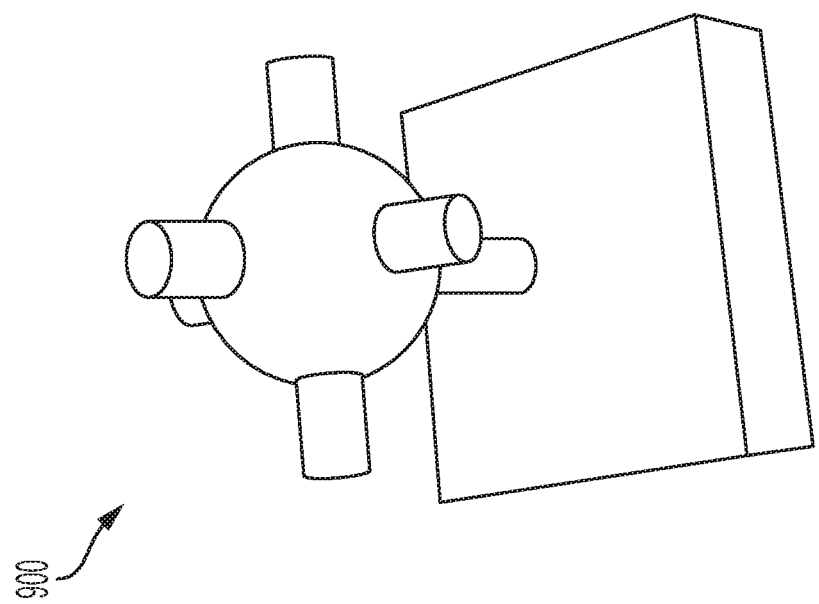
Figure 11A:
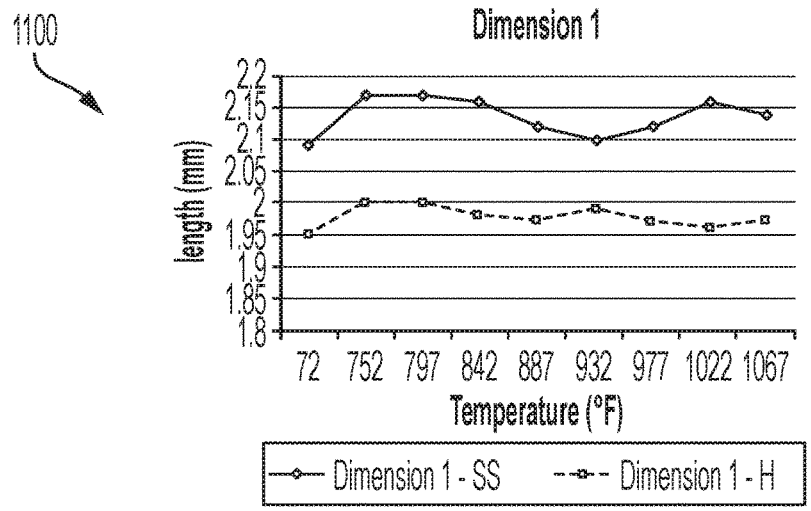
FIGS. 11A-F depict results of an experimental trial performed on the idealized aneurysm fixtures shown in FIGS. 9A-B according to an embodiment of the disclosure.
Figure 11B:
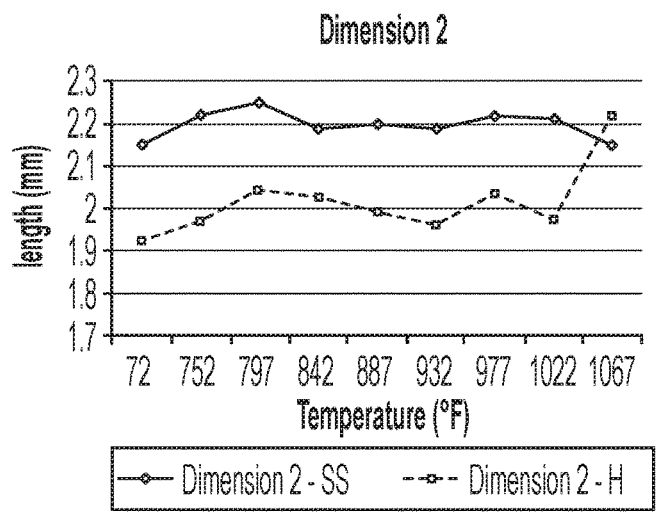
Figure 11C:
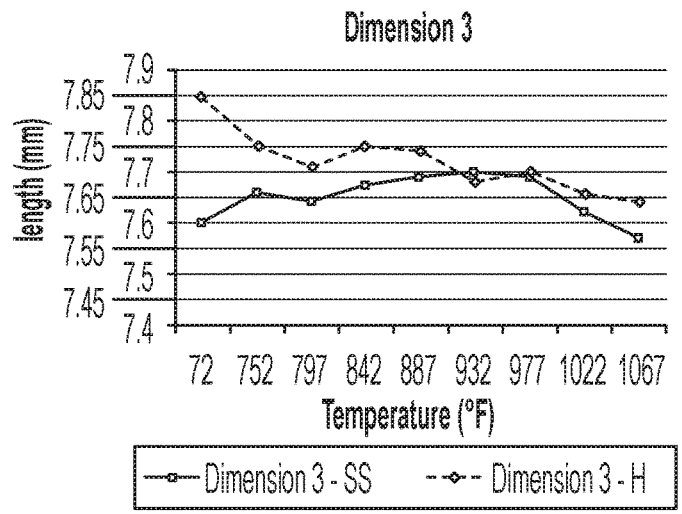
Figure 11D:
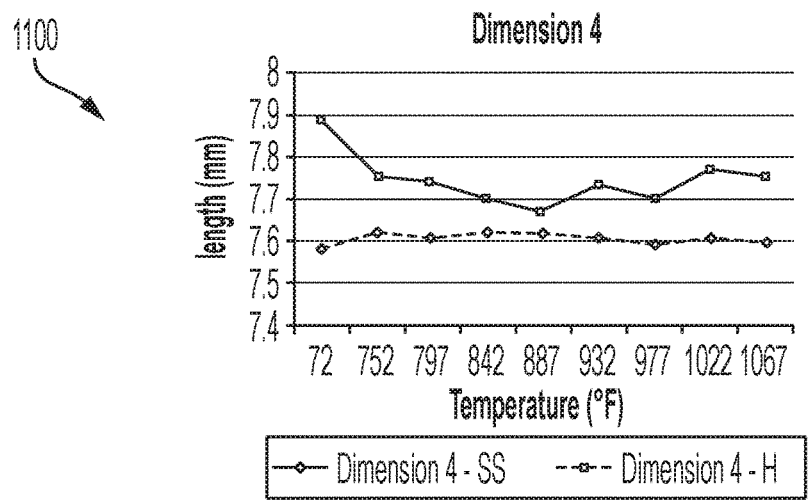
Figure 11E:
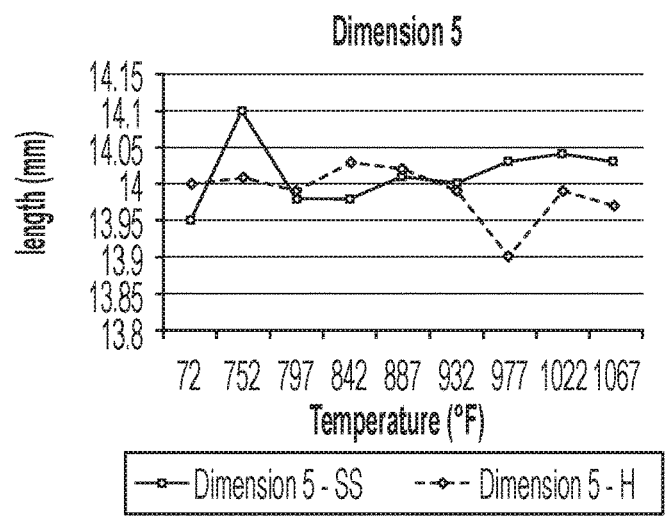
Figure 11F:
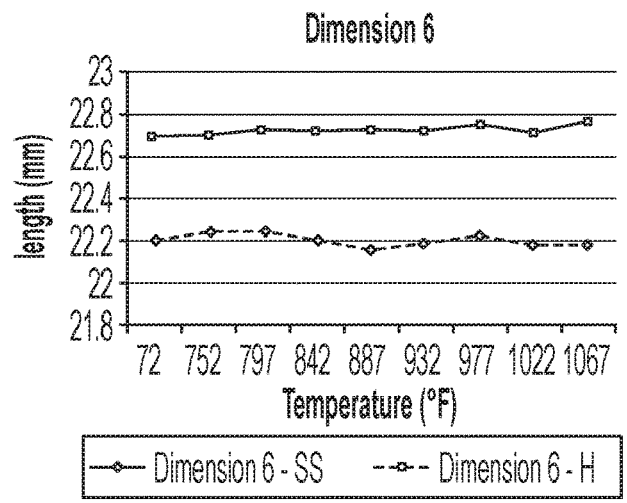

In an experimental trial of the disclosed methods, idealized figures 900 shown in FIGS. 9A-B were created. A first idealized fixture of an aneurysm was printed in 420 stainless steel infused with bronze. The fixture was accurate within +/−5% of any dimension, had one printed layer of 0.1 mm, and was heat resistant to 831° C. This fixture is shown in FIG. 9A. Another idealized fixture was printed in a Haynes superalloy. This fixture is shown in FIG. 9B. Haynes superalloys are a combination of nickel, chromium, tungsten, and molybdenum that display resilience to stresses such as temperature and strain far greater than stainless steel. For these reasons, the Haynes superalloy fixture was compared to the stainless steel fixture in preliminary temperature stress testing. The idealized fixtures each had 6 anchor cylinders at the top, bottom, and each side, all 90 degrees apart from the adjacent anchors. In the experimental trial, patient-specific fixtures based from 3D aneurysm models were printed in 316 stainless steel. The 3D printer used a class 1 laser to sinter metal powder deposited in layers in an inert gas environment and had a resolution of up to 100 micrometers depending on powder particle size. In order to experiment with creating fixtures based on the same aneurysm that could anneal coils of multiple sizes and therefore create layers of coils, the patient-specific fixture model was shrunk by 15% and 30% in all directions at the end of the design process.

To ensure the utility of the 3D printed fixtures, the idealized fixtures were evaluated on their ability to withstand the heat needed to anneal the coil that they would be used to shape set while retaining their shape and dimensions. In an experimental trial, the idealized models 900 were both evaluated on 6 different dimensions as shown in FIG. 10. These dimensions were measured before and after each heat-treatment trial. Nitinol wire is typically annealed between 450° C.-550° C., so maximum temperatures tested in each trial ranged from 400° C.-575° C. in intervals of 25° C. in order to cover a range exceeding the typical range of annealing temperatures. To recreate a nitinol shape setting process, the fixtures were placed in a kiln/oven at room temperature. The oven was then heated to each annealing temperature at the maximum ramp rate and held at that temperature for 10 minutes before the oven was opened and the fixtures were immediately cooled in water.

In the experimental trial evaluating the idealized fixtures 900, dimensions 1-5 were digitally modeled to be 2 mm, 2 mm, 7.746 mm, 7.746 mm, and 14 mm, respectively. Dimension 6 was ignored for the purpose of comparing with the digital model because the printing processes differed in regards to additions to the foundation of each fixture. The average percent error between dimensions 1-5 of the stainless steel fixture and dimensions 1-5 as designed was 3.618%, while the average percent error between dimensions 1-5 of the Haynes superalloy fixture and dimensions 1-5 as designed was 0.809%. The trial results for each fixture evaluated for each dimension are shown in FIGS. 11A-F and in TABLE 1 below.

TABLE 1

Trial 1 dimensional testing results (S.S represents stainless steel, H represents Haynes)

| Dimension | Preliminary (72° F./22° C.) | | 752° F. (400° C.) | | 797° F. (425° C.) | | 842° F. (450° C.) | | 887° F. (475° C.) | | 932° F. (500° C.) | | 977° F. (525° C.) | | 1022° F. (550° C.) | | 1067° F. (575° C.) | |
|---|---|---|---|---|---|---|---|---|---|---|---|---|---|---|---|---|---|---|
| | S.S (mm) | H (mm) | S.S (mm) | H (mm) | S.S (mm) | H (mm) | S.S (mm) | H (mm) | S.S (mm) | H (mm) | S.S (mm) | H (mm) | S.S (mm) | H (mm) | S.S (mm) | H (mm) | S.S (mm) | H (mm) |
| 1 | 2.09 | 1.95 | 2.17 | 2 | 2.17 | 2 | 2.16 | 1.98 | 2.12 | 1.97 | 2.1 | 1.99 | 2.12 | 1.97 | 2.16 | 1.96 | 2.14 | 1.97 |
| 2 | 2.15 | 1.92 | 2.22 | 1.97 | 2.25 | 2.04 | 2.19 | 2.02 | 2.2 | 1.99 | 2.19 | 1.96 | 2.22 | 2.03 | 2.21 | 1.97 | 2.15 | 2.22 |
| 3 | 7.6 | 7.85 | 7.66 | 7.75 | 7.64 | 7.71 | 7.67 | 7.75 | 7.69 | 7.74 | 7.7 | 7.68 | 7.69 | 7.7 | 7.62 | 7.66 | 7.57 | 7.64 |
| 4 | 7.89 | 7.58 | 7.75 | 7.62 | 7.74 | 7.61 | 7.7 | 7.62 | 7.67 | 7.62 | 7.73 | 7.61 | 7.7 | 7.59 | 7.77 | 7.61 | 7.75 | 7.6 |
| 5 | 13.95 | 14 | 14.1 | 14.01 | 13.98 | 13.99 | 13.98 | 14.03 | 14.01 | 14.02 | 14 | 13.99 | 14.03 | 13.9 | 14.04 | 13.99 | 14.03 | 13.97 |
| 6 | 22.7 | 22.21 | 22.7 | 22.25 | 22.73 | 22.25 | 22.72 | 22.21 | 22.73 | 22.16 | 22.72 | 22.2 | 22.75 | 22.23 | 22.71 | 22.18 | 22.77 | 22.19 |

TABLE 2 below shows the coefficient of variance for each dimension measured across all tested temperatures for each of the idealized fixtures 900.

TABLE 2

Coefficient of variance for each dimension measured across all temperatures tested in the stainless steel and Haynes fixtures used in trial 1
Coefficient of Variance

|  | Dimension 1 | Dimension 2 | Dimension 3 | Dimension 4 | Dimension 5 | Dimension 6 |
|---|---|---|---|---|---|---|
| Stainless steel | 0.014234234 | 0.01487974 | 0.005862997 | 0.008118222 | 0.003110537 | 0.001010907 |
| Haynes | 0.008762483 | 0.042870885 | 0.008089376 | 0.001859176 | 0.002709011 | 0.001377644 |

As can be seen, the measured dimensions fluctuated slightly between measurements but significant trends were not observed. The resolution of the calipers used for measurement was 0.01 mm, which is extremely precise, even in reference to aneurysms that are only a few millimeters wide. Aside from a few outlier measurements, the curve of the plot of each dimension's length plotted against temperature is fairly flat with no significant trends present over all dimensions for either part, which could indicate change in shape as temperature increase. One might expect that the variation across the part as a whole would be much less than the variation across a smaller dimension, which appears to be the case when comparing the shape of the chart shown in FIG. 11F with the shapes of the charts shown in FIGS. 11A and 11B. One notable trend is that for both fixtures in the charts shown in FIGS. 11A and 11B, the anchor points seem to expand slightly with the first 2 annealing treatments, shrink in the heat setting treatments towards the middle of the temperature range, and expand again in the annealing treatments towards the end of the temperature range. However, again, these are measurements of the anchor's width, which does not have a significant effect on the shape of a coil, and the largest difference in any measurement across either dimension over all annealing temperatures tested is only 0.1 mm. The coefficient of variance results shown in TABLE 2 support the insignificance of this variation as well, as all values are very low across all dimensions for both fixtures. The highest coefficient of variance for all of trial 1 was 0.042870885, meaning the standard deviation is roughly 4% of the average value across all temperatures for dimension 2, which was only 2 mm as designed. Human error may have contributed to these fluctuations, as the resolution of the calipers used is 0.01 mm, an extremely small measurement even in comparison to models of aneurysms that are only a few millimeters in diameter. Additionally, errors may have arisen as a result of incorrect caliper calibration. Before the preliminary measurements were taken, the caliper was zeroed at 0.00 mm, but when the caliper was returned to the 0.00 mm position following all measurements, the caliper read "−0.05 mm," which may have contributed to variance between the first preliminary measurements and corresponding measurements following annealing.

Figure 12A:
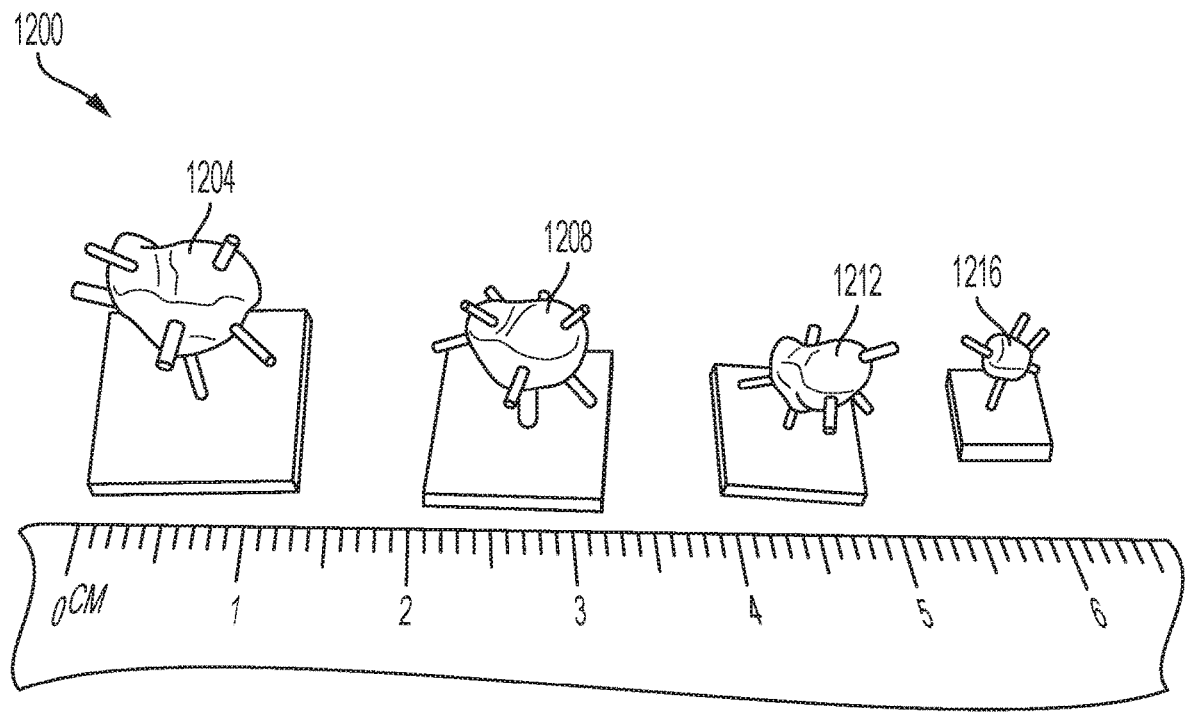
FIGS. 12A-B depict exemplary customized aneurysm fixtures that may be constructed according to an embodiment of the disclosure.
Figure 12B:
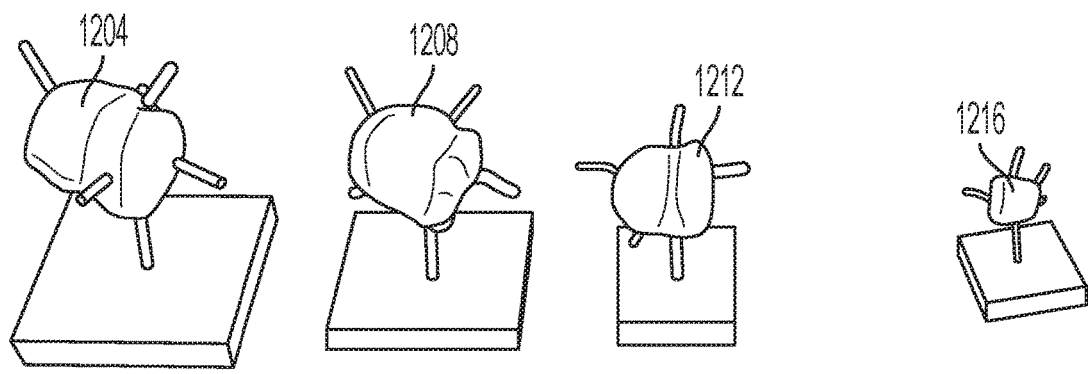
Figure 13A:
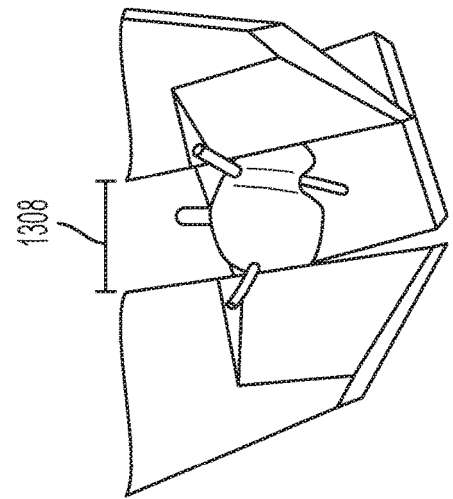
FIGS. 13A-H depict evaluation dimensions of the customized aneurysm fixtures shown in FIGS. 12A-B.
Figure 13B:
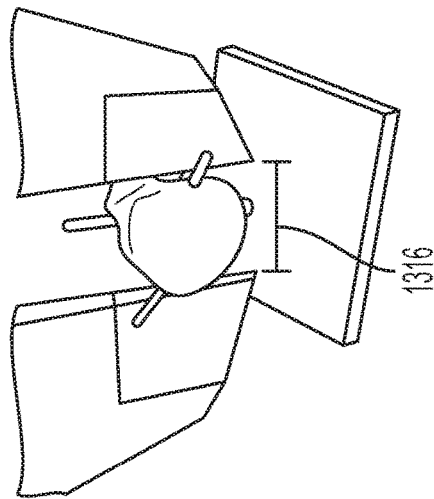
Figure 13C:
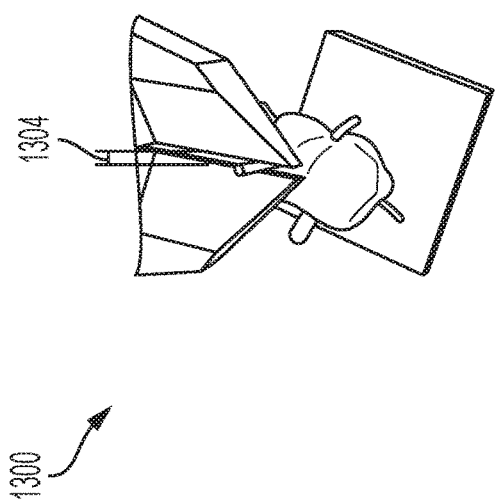
Figure 13D:
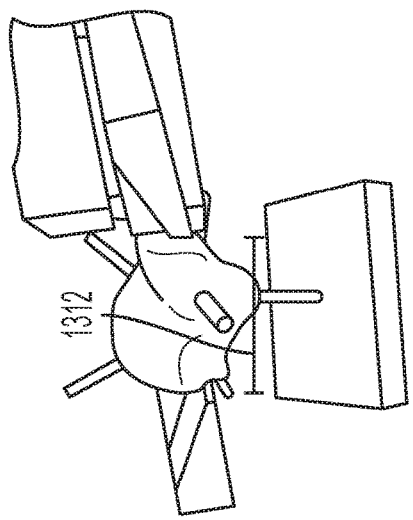
Figure 13F:
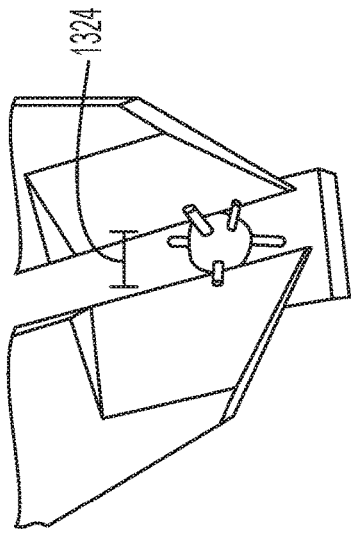
Figure 13H:
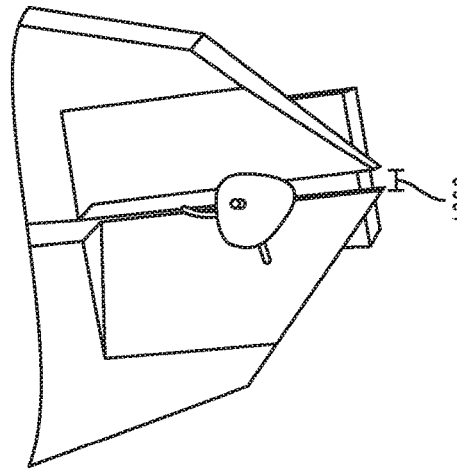
Figure 13E:
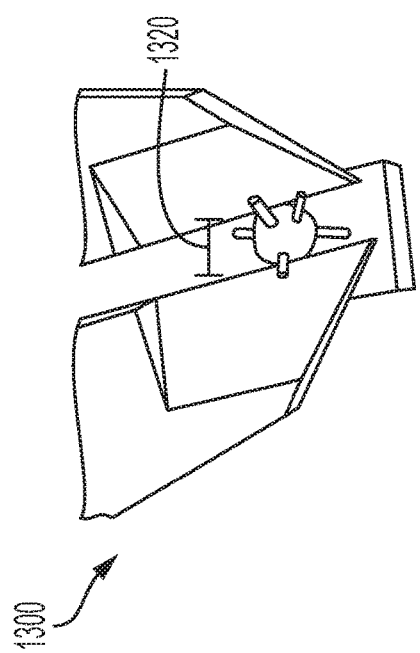
Figure 13G:
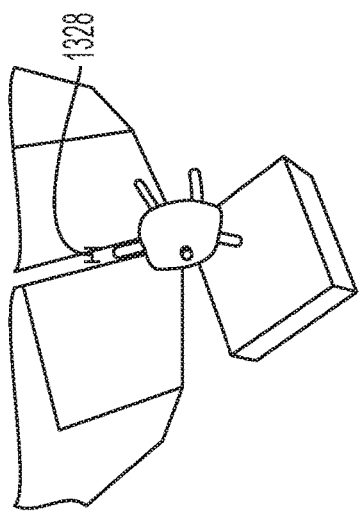
Figure 14A:
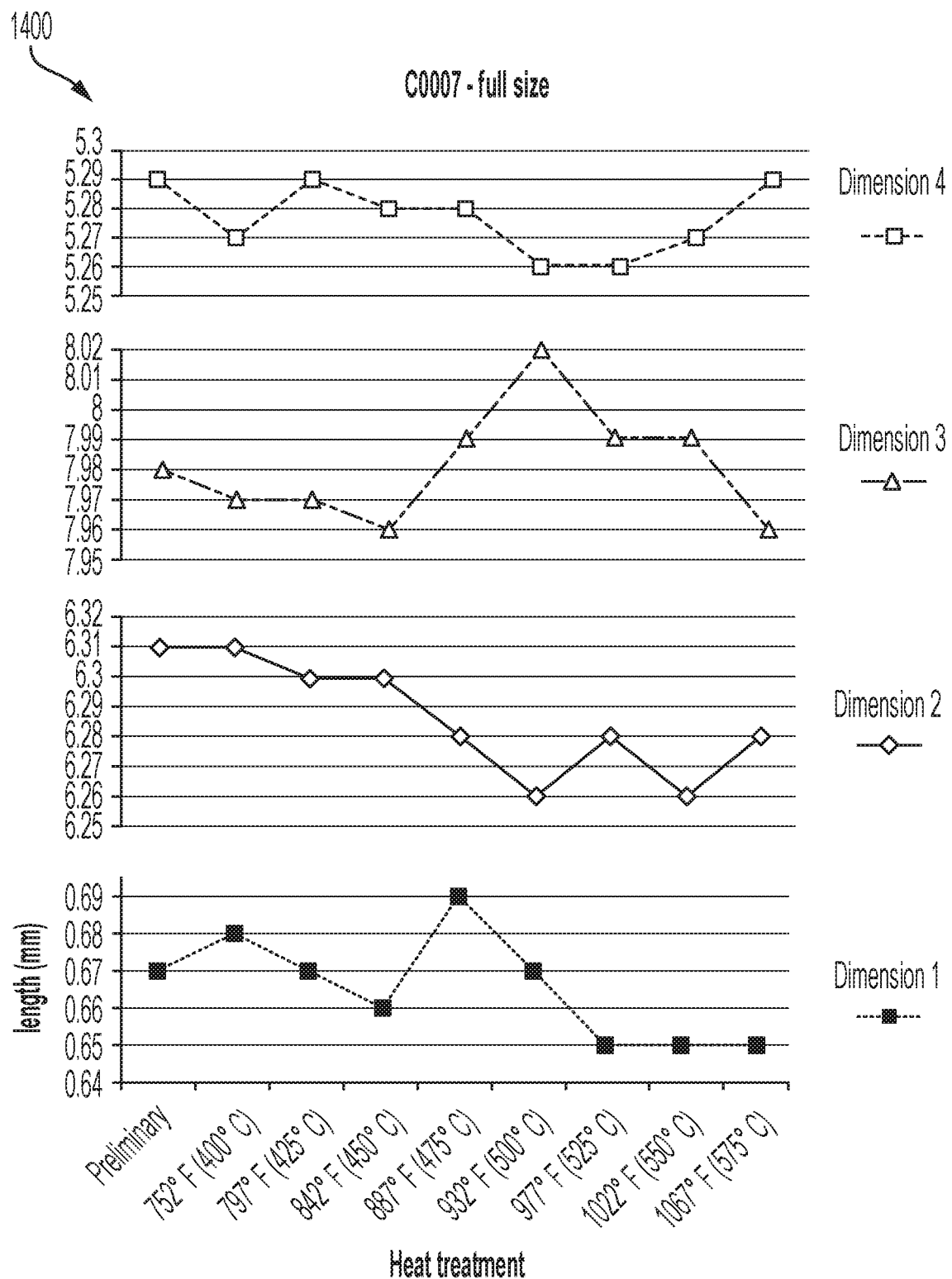
FIGS. 14A-D depict results of an experimental trial performed on the customized aneurysm fixtures shown in FIGS. 12A-B according to an embodiment of the disclosure.
Figure 14B:
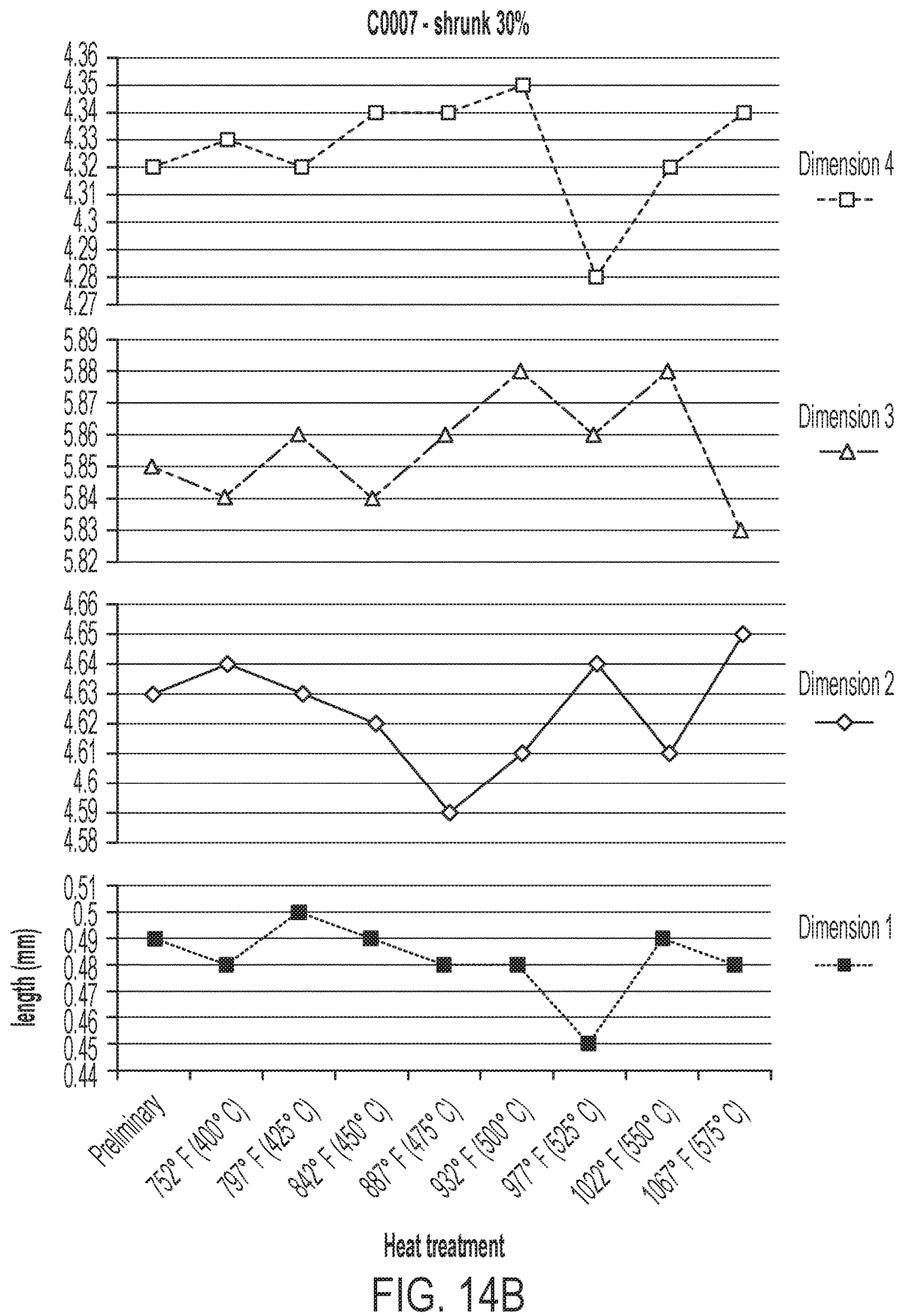
Figure 14C:
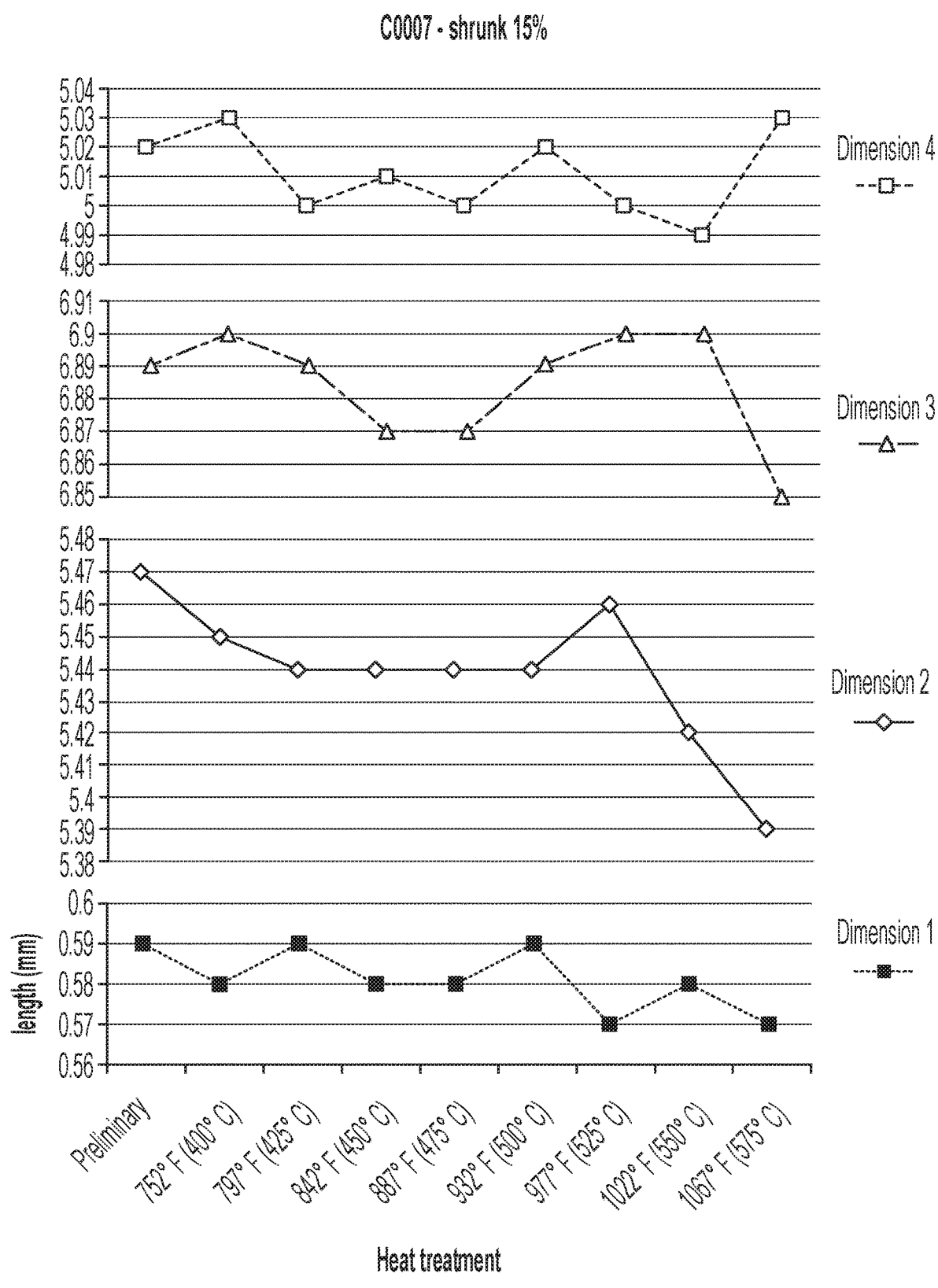
Figure 14D:
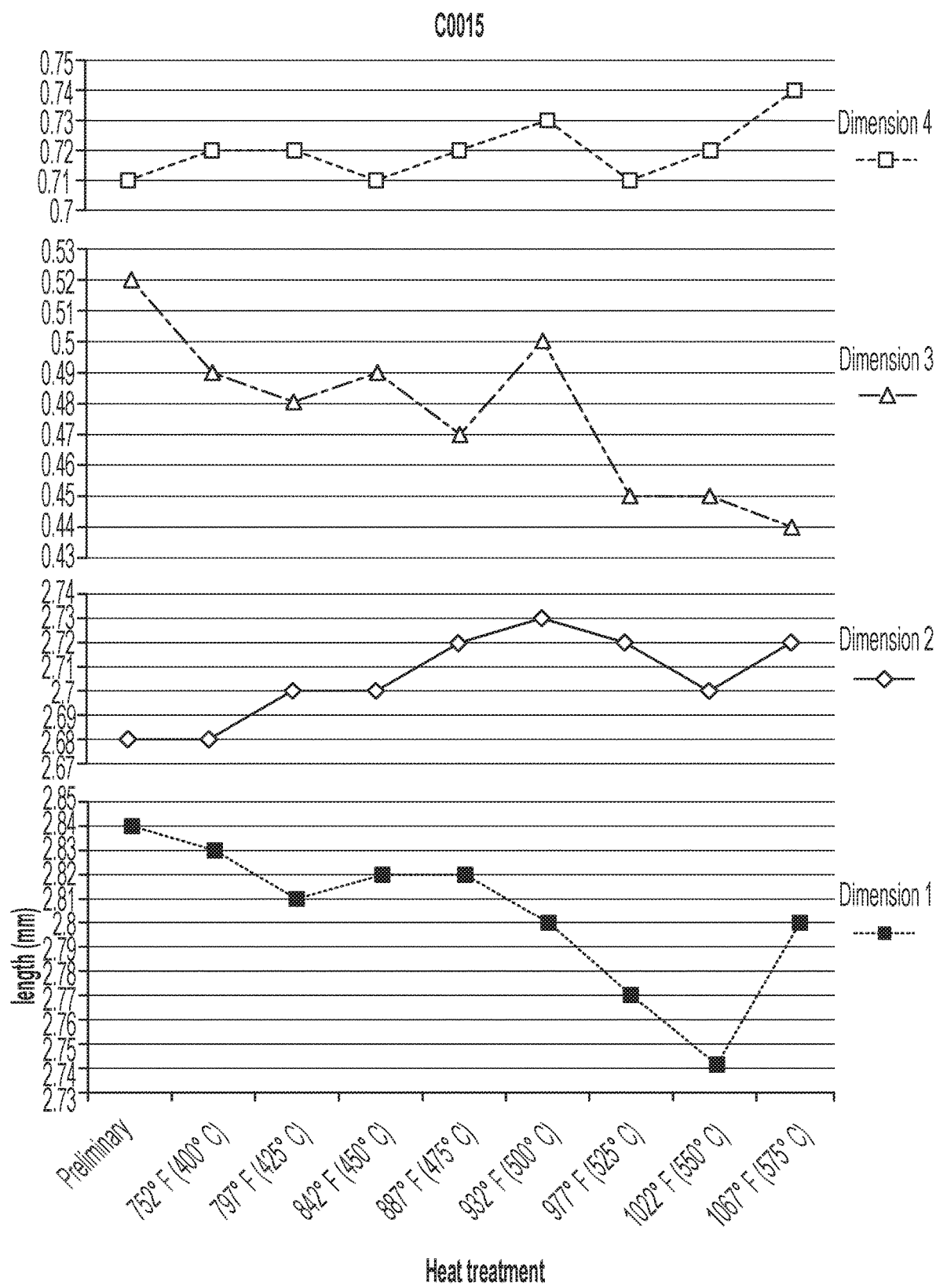

In the experimental trial evaluating the patient-specific fixtures, fixtures 1200 shown in FIGS. 12A-B modeled after two patient-specific aneurysms were tested and evaluated at the dimensions 1300 shown in FIGS. 13A-H. In the embodiment shown, fixture 1204 is modeled after a first patient-specific aneurysm, fixture 1208 is a model of the aneurysm of 1204 shrunk 15%, and fixture 1212 is a model of the aneurysm of 1204 shrunk 30%. Fixture 1216 is modeled after a second patient-specific aneurysm. FIG. 12A shows fixtures 1200 after 3D printing but before testing and FIG. 12B shows fixtures 1200 after testing. In the embodiments shown, dimensions 1304, 1308, 1312, and 1316 of FIGS. 13A-D correspond to dimensions 1-4, respectively, measured for fixtures 1204, 1208, and 1212. In the embodiments shown, dimensions 1320, 1324, 1328, and 1332 of FIGS. 13E-H correspond to dimensions 1-4, respectively, measured for fixture 1216. The trial results 1400 for fixtures 1200 are shown in FIGS. 14A-D and in TABLE 3 below.

TABLE 3

Trial 2 dimensional testing results (7a represents fixture 1204, 7b represents fixture 1208, 7c represents fixture 1212, and 15 represents fixture 1216)

| Dimension | 7a (mm) | 7b (mm) | 7c (mm) | 15 (mm) | 7a (mm) | 7b (mm) | 7c (mm) | 15 (mm) | 7a (mm) | 7b (mm) | 7c (mm) | 15 (mm) |
|---|---|---|---|---|---|---|---|---|---|---|---|---|
| | Preliminary (72° F./22° C.) | | | | 752° F. (400° C.) | | | | 797° F. (425° C.) | | | |
| 1 | 0.67 | 0.59 | 0.49 | 2.84 | 0.68 | 0.58 | 0.48 | 2.83 | 0.67 | 0.59 | 0.50 | 2.81 |
| 2 | 6.31 | 5.47 | 4.63 | 2.68 | 6.31 | 5.45 | 4.64 | 2.68 | 6.30 | 5.44 | 4.63 | 2.70 |
| 3 | 7.98 | 6.89 | 5.85 | 0.52 | 7.97 | 6.90 | 5.84 | 0.49 | 7.97 | 6.89 | 5.86 | 0.48 |
| 4 | 5.29 | 5.02 | 4.32 | 0.71 | 5.27 | 5.03 | 4.33 | 0.72 | 5.29 | 5.00 | 4.32 | 0.72 |
| | 842° F. (450° C.) | | | | 887° F. (475° C.) | | | | 932° F. (500° C.) | | | |
| 1 | 0.66 | 0.58 | 0.49 | 2.82 | 0.69 | 0.58 | 0.48 | 2.82 | 0.67 | 0.59 | 0.48 | 2.80 |
| 2 | 6.30 | 5.44 | 4.62 | 2.70 | 6.28 | 5.44 | 4.59 | 2.72 | 6.26 | 5.44 | 4.61 | 2.73 |
| 3 | 7.96 | 6.87 | 5.84 | 0.49 | 7.99 | 6.87 | 5.86 | 0.47 | 8.02 | 6.89 | 5.88 | 0.50 |
| 4 | 5.28 | 5.01 | 4.34 | 0.71 | 5.28 | 5.00 | 4.34 | 0.72 | 5.26 | 5.02 | 4.35 | 0.73 |
| | 977° F. (525° C.) | | | | 1022° F. (550° C.) | | | | 1067° F. (575° C.) | | | |
| 1 | 0.65 | 0.57 | 0.45 | 2.77 | 0.65 | 0.58 | 0.49 | 2.74 | 0.65 | 0.57 | 0.48 | 2.8 |
| 2 | 6.28 | 5.46 | 4.64 | 2.72 | 6.26 | 5.42 | 4.61 | 2.7 | 6.28 | 5.39 | 4.65 | 2.72 |
| 3 | 7.99 | 6.9 | 5.86 | 0.45 | 7.99 | 6.9 | 5.88 | 0.45 | 7.96 | 6.85 | 5.83 | 0.44 |
| 4 | 5.26 | 5 | 4.28 | 0.71 | 5.27 | 4.99 | 4.32 | 0.72 | 5.29 | 5.03 | 4.34 | 0.74 |

TABLE 4 below shows the coefficient of variance for each dimension measured across all tested temperatures for each of the patient-specific fixtures 1200.

TABLE 4

Coefficient of variance for each dimension measured across all temperatures tested for each fixture tested in trial 2
Coefficient of Variance

|  | Dimension 1 | Dimension 2 | Dimension 3 | Dimension 4 |
|---|---|---|---|---|
| C0007 (full size) | 0.021395669 | 0.003080315 | 0.002380987 | 0.002321058 |
| C0007 (shrunk 15%) | 0.013452435 | 0.004257133 | 0.002527511 | 0.002899489 |
| C0007 (shrunk 30%) | 0.028916821 | 0.004061543 | 0.002971624 | 0.00476476 |
| C0015 | 0.011138522 | 0.006691651 | 0.055505272 | 0.013888889 |

As can be seen, the measurements for each dimension varied slightly across all temperatures tested without great significance. The measured dimensions varied a few hundredths of millimeters between trials but without significant trends seen. One interesting trend is that in all fixtures based off of fixture 1204 (aneurisk sample C0007) at dimension 3, which is essentially the maximum width of the fixture, the measurements trend downwards towards the end of the trial, with the measurement after heat setting at 1067° F. (575° C.) being the lowest observed measurement. However, the difference between measurements remains insignificant as the coefficient of variance remains below 0.003 for dimension 3 in those three fixtures. Just as in trial 1, the coefficients of variance for trial 2 were all very low for all dimensions of all fixtures, with only 6 of 16 coefficients of variance being higher than 0.01. The highest coefficient of variance observed is 0.055505272 for dimension 3 for fixture 1216 (based off of aneurisk sample C0015). This dimension is of the width of one of the anchors, which was measured as only 0.52 mm wide prior to heat-treating, and has little to no effect on the effectiveness of any coil annealed on such a fixture. Once again, human error during measurement is a likely contributor to this variation, which could be reduced with multiple people taking measurements that would then be averaged for each dimension at each temperature. Additionally, most graphs appear to have a negative overall slope if one can even be observed. If the shapes of the fixtures were to change with any significance while annealing nitinol on them, a decrease in size would be preferred over an increase in size, because an increase in size could cause a coil to be larger than expected and rupture the aneurysm during delivery if it pushes against the wall of the aneurysm, while a decrease in size of the coil would only cause occlusion to be slightly less effective.

Figure 15B:
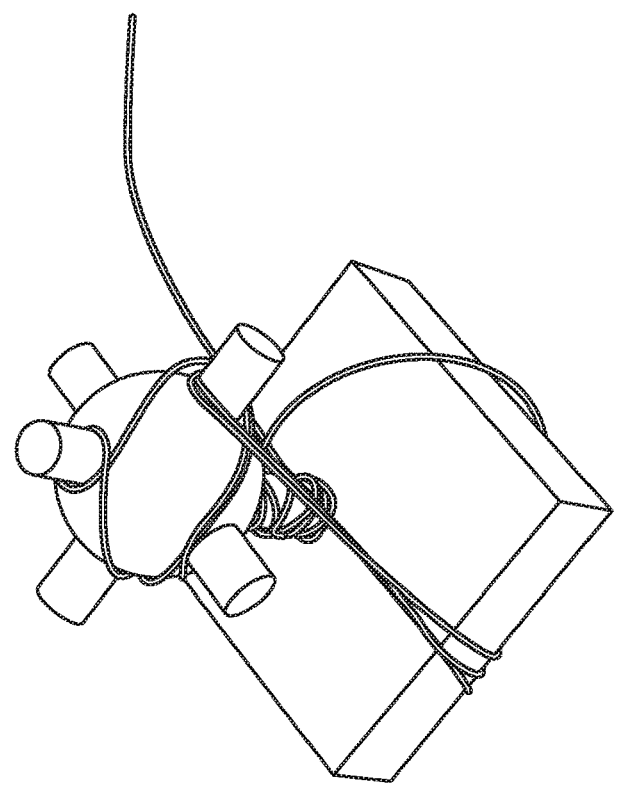
FIGS. 15A-B depict exemplary coils wrapped around exemplary aneurysm fixtures that may be constructed according to an embodiment of the disclosure.
Figure 15A:
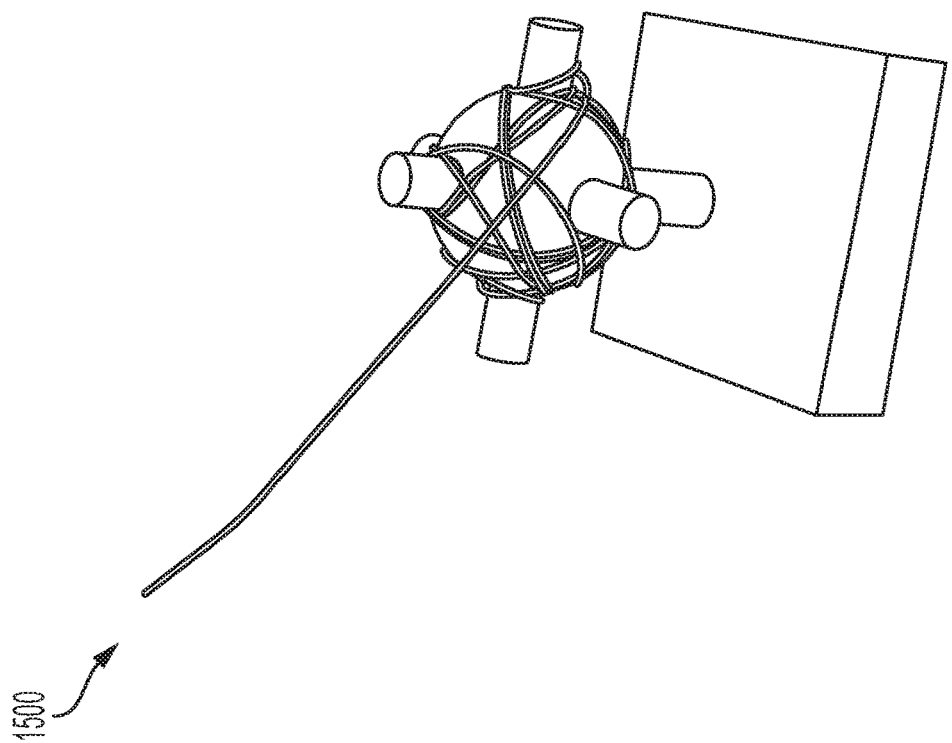

FIGS. 15A-B show exemplary coils 1500 created by wrapping around annealed fixtures of aneurysms. In the embodiment shown, coils 1500 can be made of nitinol but other suitable coil materials, as discussed above, can also be used, such as any shape memory alloy. Nitinol is a unique shape memory alloy made of nickel and titanium that also possesses superelasticity and biocompatibility qualities. Superelasticity refers to the fact that nitinol can be deformed significantly and recover its original shape without damage to the crystal structure of the material, and biocompatibility refers to the fact that the material can be implanted in vivo for extended periods of time without significant complications. Nitinol exists in two phases, with Martensite being the lower temperature phase of and Austenite being the higher temperature phase. Raw nitinol can be fixed into a desired position and heated to an annealing temperature, often around 500° C. (932° F.). This causes the nitinol to "remember" this austenitic shape, so that when it is cooled to Martensite, it can be manipulated and deformed into various positions, but when reheated past a certain transition temperature, it will return to its "remembered" austenitic shape.

As shown in FIGS. 15A-B, nitinol wire can be wrapped around the fixture and secured by feeding each end of the wire under a wire portion tightly wound around the fixture. In the embodiment shown in FIG. 15A, the wire was wrapped around the spherical "aneurysm" portion of the fixture using the anchor points as pivots to cover each aspect of the spherical body. In this way, the coil takes the shape of the spherical "aneurysm" body and can be annealed in this position to retain the aneurysm shape. In the embodiment shown in FIG. 15B, a more complex wrapping pattern was followed using all portions of the fixture in order to observe the behavior of coil set in a more complex and irregular shape. In an experimental trial, the fixtures and wrapped coils shown were placed in an oven at room temperature. The oven was heated to a maximum temperature of 932° F. (500° C.) at the maximum ramp rate where it was held for 10 minutes before the fixtures were removed and immediately cooled in water. The nitinol coils were then unwound from the fixtures by hand with care not to stress the nitinol or fixture more than necessary and let rest at room temperature to observe any gradual transformations in shape.

Figure 16:
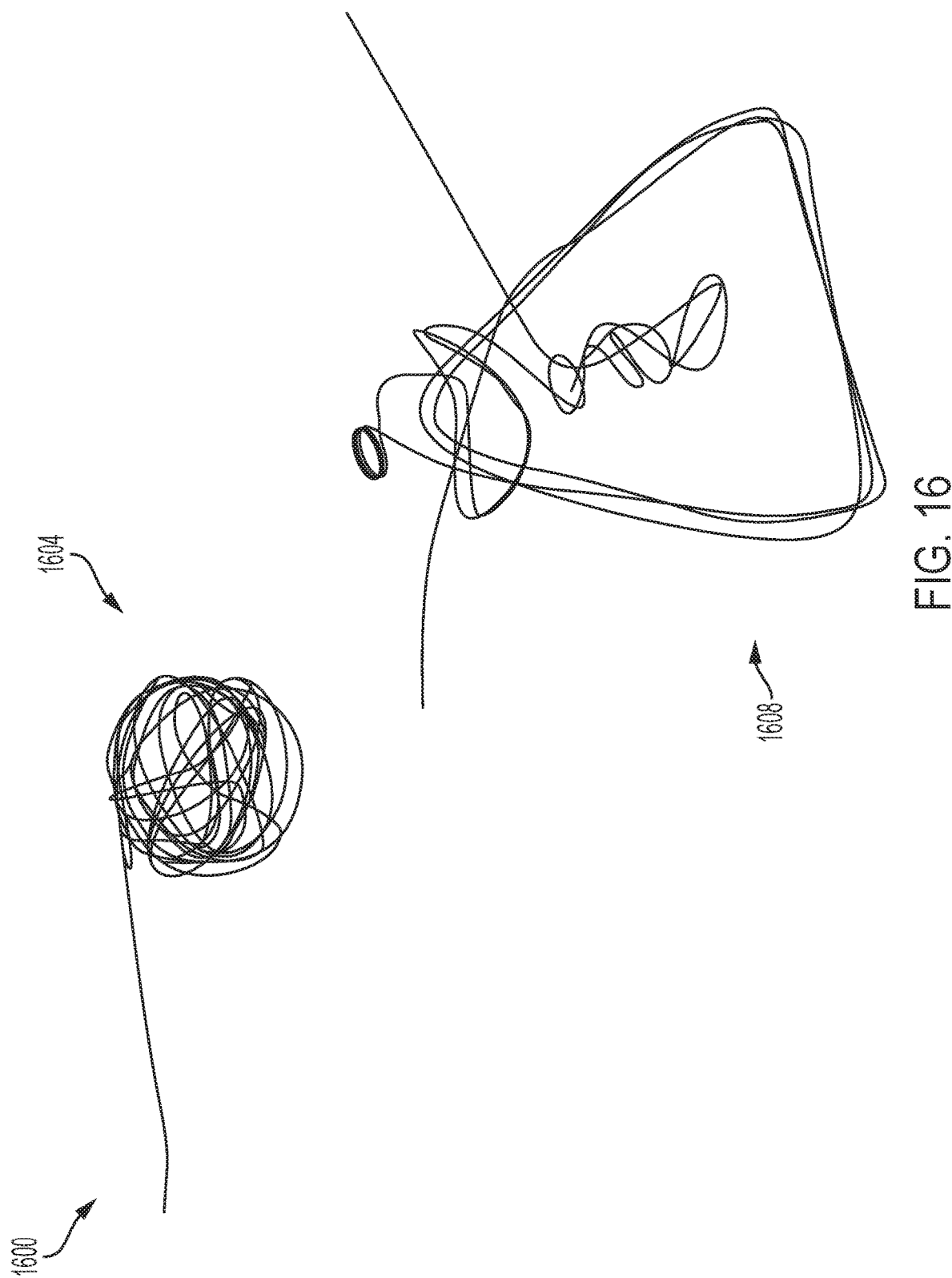
FIG. 16 depicts the exemplary coils constructed in FIGS. 15A-B after removal from the exemplary aneurysm fixtures according to an embodiment of the disclosure.

The experimental nitinol coil shape setting trial discussed above returned positive results, as shown by comparing the fixtures wound around the fixtures shown in FIGS. 15A-B with the nitinol coils 1600 removed from the fixtures after annealing as shown in FIG. 16. In the embodiment shown, coil 1604 corresponds to the coil wound around the fixture shown in FIG. 15A and coil 1608 corresponds to the coil wound around the fixture shown in FIG. 15B. As shown, the reheated nitinol coils 1604, 1608 returned to the shapes they were wound into after they were quenched and removed from the fixtures. The nitinol appeared to be in its Austenite phase after resting at room temperature, as it returned to the coiled shape when stretched. The wires returned to the shapes they were wound into after stretching.

All of the apparatuses and methods disclosed and claimed herein can be made and executed without undue experimentation in light of the present disclosure. While the compositions and methods of this invention have been described in terms of preferred embodiments, it will be apparent to those of skill in the art that variations may be applied to the apparatuses and methods and in the steps or in the sequence of steps of the method described herein without departing from the concept, spirit and scope of the invention. More specifically, it will be apparent that certain compositions which are related may be substituted for the compositions described herein while the same or similar results would be achieved. All such similar substitutes and modifications apparent to those skilled in the art are deemed to be within the spirit, scope and concept of the invention as defined by the appended claims.

What is claimed is:

1. A patient-specific endovascular coil with a patient-specific fixture and adapted for the treatment of an aneurysm in a specific patient and/or population of patients having a similar aneurysm shape and size, wherein a highest coefficient of variance for a dimension of the patient-specific fixture when the patient-specific fixture is tested across a range of temperatures is below 0.003, and wherein the patient-specific fixture is customized to be patient-specific based on:

a shape and size of the aneurysm in the specific patient; and/or the aneurysm shape and size that is similar for the population of patients.

2. The patient-specific endovascular coil of claim 1, further defined as a 3D complex coil comprising wire.

3. The patient-specific endovascular coil of claim 2, wherein the wire comprises nitinol, platinum:tungsten, and/or platinum:iridium.

4. The patient-specific endovascular coil of claim 1, wherein the patient-specific endovascular coil comprises a shape memory alloy.

5. The patient-specific endovascular coil of claim 1, further defined as being produced by a method comprising 3D printing or a casting technique.

6. The patient-specific endovascular coil of claim 1, further defined as being produced for the specific patient based on a modeling of data from that specific patient.

7. A method of treating an aneurysm in a patient, the method comprising:
   obtaining the patient-specific endovascular coil with the patient-specific fixture of claim 1; and
   inserting the coil into the patient.

8. The method of claim 7, wherein the inserting is by a microcatheter.

* * * * *